United States Patent
Fright et al.

(10) Patent No.: US 11,850,025 B2
(45) Date of Patent: *Dec. 26, 2023

(54) HANDHELD SKIN MEASURING OR MONITORING DEVICE

(71) Applicant: Aranz Healthcare Limited, Christchurch (NZ)

(72) Inventors: William Richard Fright, Christchurch (NZ); Brent Stephen Robinson, Christchurch (NZ); Shane Robert Goodwin, Christchurch (NZ); Bruce Clinton McCallum, Little River (CH); Philip John Barclay, Christchurch (NZ)

(73) Assignee: Aranz Healthcare Limited

( * ) Notice: Subject to any disclaimer, the term of this patent is extended or adjusted under 35 U.S.C. 154(b) by 440 days.

This patent is subject to a terminal disclaimer.

(21) Appl. No.: 17/100,615

(22) Filed: Nov. 20, 2020

(65) Prior Publication Data

US 2021/0068664 A1 Mar. 11, 2021

Related U.S. Application Data

(63) Continuation of application No. 15/851,580, filed on Dec. 21, 2017, now Pat. No. 10,874,302, which is a
(Continued)

(51) Int. Cl.
*A61B 5/00* (2006.01)

(52) U.S. Cl.
CPC .......... *A61B 5/0077* (2013.01); *A61B 5/0013* (2013.01); *A61B 5/444* (2013.01);
(Continued)

(58) Field of Classification Search
CPC ..... A61B 5/0077; A61B 5/0013; A61B 5/444; A61B 5/445; A61B 2560/0425;
(Continued)

(56) References Cited

U.S. PATENT DOCUMENTS

| | | |
|---|---|---|
| 3,259,612 A | 7/1966 | Peter |
| 3,335,716 A | 8/1967 | Alt et al. |
| (Continued) | | |

FOREIGN PATENT DOCUMENTS

| | | |
|---|---|---|
| AT | 549703 | 3/2012 |
| CN | 110326029 | 10/2019 |
| (Continued) | | |

OTHER PUBLICATIONS

Dowsett, C. et al., "Triangle of Wound Assessment—made easy", Wounds Asia (www.woundasia.com), May 2015.
(Continued)

*Primary Examiner* — Joel Lamprecht
(74) *Attorney, Agent, or Firm* — Perkins Coie LLP

(57) ABSTRACT

A handheld skin monitoring or measuring device includes a camera having a camera optical axis; and a structured light arrangement configured to project three or more laser fan beams such that the laser fan beams cross at a crossing point in front of the camera.

4 Claims, 16 Drawing Sheets

Related U.S. Application Data continuation of application No. 14/931,465, filed on Nov. 3, 2015, now Pat. No. 9,861,285, which is a continuation of application No. 13/686,738, filed on Nov. 27, 2012, now Pat. No. 9,179,844.

(60) Provisional application No. 61/564,089, filed on Nov. 28, 2011.

(52) U.S. Cl.
CPC ........... *A61B 5/445* (2013.01); *H05K 999/99* (2013.01); *A61B 2560/0425* (2013.01); *A61B 2560/0431* (2013.01); *A61B 2562/0233* (2013.01)

(58) Field of Classification Search
CPC .... A61B 2560/0431; A61B 2562/0233; H05K 999/99
See application file for complete search history.

(56) References Cited

U.S. PATENT DOCUMENTS

| | | |
|---|---|---|
| 4,090,501 A | 5/1978 | Chaitin |
| 4,170,987 A | 10/1979 | Anselmo et al. |
| 4,236,082 A | 11/1980 | Butler |
| 4,505,583 A | 3/1985 | Konomi |
| 4,515,165 A | 5/1985 | Carroll |
| 4,535,782 A | 8/1985 | Zoltan |
| 4,556,057 A | 12/1985 | Hiruma et al. |
| 4,724,480 A | 2/1988 | Hecker et al. |
| 4,736,739 A | 4/1988 | Flaton |
| 4,768,513 A | 9/1988 | Suzuki |
| 4,773,097 A | 9/1988 | Suzaki et al. |
| 4,821,117 A | 4/1989 | Sekiguchi |
| 4,839,807 A | 6/1989 | Doi et al. |
| 4,851,984 A | 7/1989 | Doi et al. |
| 4,894,547 A | 1/1990 | Leffell et al. |
| 4,930,516 A | 6/1990 | Alfano et al. |
| 4,957,114 A | 9/1990 | Zeng et al. |
| 4,979,815 A | 12/1990 | Tsikos |
| 4,996,994 A | 3/1991 | Steinhauer et al. |
| D315,901 S | 4/1991 | Knowles |
| 5,003,977 A | 4/1991 | Suzuki et al. |
| 5,016,173 A | 5/1991 | Kenet et al. |
| 5,036,853 A | 8/1991 | Jeffcoat et al. |
| 5,080,100 A | 1/1992 | Trotel |
| 5,157,461 A | 10/1992 | Page |
| 5,174,297 A | 12/1992 | Daikuzono |
| 5,241,468 A | 8/1993 | Kenet |
| 5,270,168 A | 12/1993 | Grinnell |
| 5,319,550 A | 6/1994 | Griffith |
| 5,363,854 A | 11/1994 | Martens et al. |
| 5,369,496 A | 11/1994 | Alfano et al. |
| 5,396,331 A | 3/1995 | Kitoh et al. |
| 5,408,996 A | 4/1995 | Salb |
| 5,421,337 A | 6/1995 | Richards-Kortum et al. |
| 5,515,449 A | 5/1996 | Tsuruoka et al. |
| 5,519,208 A | 5/1996 | Esparza et al. |
| 5,528,703 A | 6/1996 | Lee |
| 5,531,520 A | 7/1996 | Grimson et al. |
| 5,532,824 A | 7/1996 | Harvey et al. |
| 5,561,526 A | 10/1996 | Huber et al. |
| 5,588,428 A | 12/1996 | Smith et al. |
| 5,590,660 A | 1/1997 | MacAulay et al. |
| 5,603,318 A | 2/1997 | Heilbrun et al. |
| 5,627,907 A | 5/1997 | Gur et al. |
| 5,644,141 A | 7/1997 | Hooker et al. |
| 5,648,915 A | 7/1997 | McKinney et al. |
| 5,673,300 A | 9/1997 | Reckwerdt et al. |
| 5,689,575 A | 11/1997 | Sako et al. |
| 5,699,798 A | 12/1997 | Hochman et al. |
| 5,701,902 A | 12/1997 | Vari et al. |
| 5,717,791 A | 2/1998 | Labaere et al. |
| D393,068 S | 3/1998 | Kodama |
| 5,740,268 A | 4/1998 | Nishikawa et al. |
| 5,749,830 A | 5/1998 | Kaneko et al. |
| 5,784,162 A | 7/1998 | Cabib et al. |
| 5,791,346 A | 8/1998 | Craine et al. |
| 5,799,100 A | 8/1998 | Clarke et al. |
| 5,810,014 A | 9/1998 | Davis et al. |
| 5,836,872 A | 11/1998 | Kenet et al. |
| 5,910,972 A | 6/1999 | Ohkubo et al. |
| 5,921,937 A | 7/1999 | Davis et al. |
| 5,946,645 A | 8/1999 | Rioux et al. |
| 5,957,837 A | 9/1999 | Raab |
| 5,967,797 A | 10/1999 | Maldonado |
| 5,967,979 A | 10/1999 | Taylor et al. |
| 5,969,822 A | 10/1999 | Fright et al. |
| 5,974,165 A | 10/1999 | Giger et al. |
| 6,032,070 A | 2/2000 | Flock et al. |
| 6,081,612 A | 6/2000 | Gutkowicz-Krusin et al. |
| 6,081,739 A | 6/2000 | Lemchen |
| 6,091,995 A | 7/2000 | Ingle et al. |
| 6,101,408 A | 8/2000 | Craine et al. |
| 6,208,749 B1 | 3/2001 | Gutkowicz-Krusin et al. |
| 6,215,893 B1 | 4/2001 | Leshem et al. |
| 6,265,151 B1 | 7/2001 | Canter et al. |
| 6,266,453 B1 | 7/2001 | Hibbard et al. |
| 6,272,278 B1 | 8/2001 | Takahata et al. |
| 6,278,793 B1 | 8/2001 | Gur et al. |
| 6,307,957 B1 | 10/2001 | Gutkowicz-Krusin et al. |
| 6,324,417 B1 | 11/2001 | Cotton |
| D453,350 S | 2/2002 | Fenton |
| 6,359,513 B1 | 3/2002 | Kuo et al. |
| 6,359,612 B1 | 3/2002 | Peter |
| D455,166 S | 4/2002 | Raad |
| 6,381,026 B1 | 4/2002 | Schiff et al. |
| 6,381,488 B1 | 4/2002 | Dickey et al. |
| 6,392,744 B1 | 5/2002 | Holec |
| 6,396,270 B1 | 5/2002 | Smith |
| 6,413,212 B1 | 7/2002 | Raab |
| 6,421,463 B1 | 7/2002 | Poggio et al. |
| 6,427,022 B1 | 7/2002 | Craine et al. |
| 6,491,632 B1 | 12/2002 | Taylor |
| 6,567,682 B1 | 5/2003 | Osterweil et al. |
| 6,594,388 B1 | 7/2003 | Gindele et al. |
| 6,594,516 B1 | 7/2003 | Steckner et al. |
| 6,603,552 B1 | 8/2003 | Cline et al. |
| 6,611,617 B1 | 8/2003 | Crampton |
| 6,611,833 B1 | 8/2003 | Johnson |
| 6,631,286 B2 | 10/2003 | Pfeiffer et al. |
| 6,648,820 B1 | 11/2003 | Sarel |
| 6,671,349 B1 | 12/2003 | Griffith |
| 6,678,001 B1 | 1/2004 | Elberbaum |
| 6,690,964 B2 | 2/2004 | Bieger et al. |
| 6,715,675 B1 | 4/2004 | Rosenfeld |
| 6,754,370 B1 | 6/2004 | Hall-Holt et al. |
| 6,770,186 B2 | 8/2004 | Rosenfeld et al. |
| 6,798,571 B2 | 9/2004 | Wetzel et al. |
| 6,809,803 B1 | 10/2004 | O'Brien et al. |
| 6,810,279 B2 | 10/2004 | Mansfield et al. |
| 6,816,606 B2 | 11/2004 | Wetzel et al. |
| 6,816,847 B1 | 11/2004 | Toyama |
| 6,862,410 B2 | 3/2005 | Miyoshi |
| 6,862,542 B2 | 3/2005 | Lockhart et al. |
| 6,873,340 B2 | 3/2005 | Luby |
| 6,873,716 B1 | 3/2005 | Bowker |
| 6,879,394 B2 | 4/2005 | Amblard et al. |
| 6,907,193 B2 | 6/2005 | Kollias et al. |
| 6,915,073 B2 | 7/2005 | Seo |
| 6,922,523 B2 | 7/2005 | Merola et al. |
| 6,941,323 B1 | 9/2005 | Galperin |
| 6,961,517 B2 | 11/2005 | Merola et al. |
| 6,968,094 B1 | 11/2005 | Gallagher |
| 6,993,169 B2 | 1/2006 | Wetzel et al. |
| 7,006,223 B2 | 2/2006 | Mullani |
| 7,013,172 B2 | 3/2006 | Mansfield et al. |
| 7,015,906 B2 | 3/2006 | Olschewski et al. |
| 7,027,153 B2 | 4/2006 | Mullani |
| 7,040,536 B2 | 5/2006 | Rosenfeld |
| 7,054,674 B2 | 5/2006 | Cane et al. |
| 7,064,311 B2 | 6/2006 | Jung et al. |
| 7,068,828 B2 | 6/2006 | Kim et al. |

(56) References Cited

U.S. PATENT DOCUMENTS

| | | | |
|---|---|---|---|
| 7,068,836 B1 | 6/2006 | Rubbert et al. |
| 7,074,509 B2 | 7/2006 | Rosenfeld et al. |
| 7,103,205 B2 | 9/2006 | Wang et al. |
| 7,106,885 B2 | 9/2006 | Osterweil et al. |
| 7,127,094 B1 | 10/2006 | Elbaum et al. |
| 7,127,280 B2 | 10/2006 | Dauga |
| 7,128,894 B1 | 10/2006 | Tannous et al. |
| 7,130,465 B2 | 10/2006 | Muenzenmayer et al. |
| 7,136,191 B2 | 11/2006 | Kaltenbach et al. |
| D533,555 S | 12/2006 | Odhe et al. |
| 7,155,049 B2 | 12/2006 | Wetzel et al. |
| 7,162,063 B1 | 1/2007 | Craine et al. |
| 7,167,243 B2 | 1/2007 | Mullani |
| 7,167,244 B2 | 1/2007 | Mullani |
| 7,181,363 B2 | 2/2007 | Ratti et al. |
| 7,194,114 B2 | 3/2007 | Schneiderman |
| 7,212,660 B2 | 5/2007 | Wetzel et al. |
| 7,227,621 B2 | 6/2007 | Lee et al. |
| 7,233,693 B2 | 6/2007 | Momma |
| D547,347 S | 7/2007 | Kim |
| 7,248,724 B2 | 7/2007 | Gutenev |
| D554,682 S | 11/2007 | Martinez |
| 7,295,226 B1 | 11/2007 | Meron et al. |
| 7,298,881 B2 | 11/2007 | Giger et al. |
| D561,804 S | 2/2008 | Asai |
| 7,347,365 B2 | 3/2008 | Rowe |
| 7,376,346 B2 | 5/2008 | Merola et al. |
| 7,400,754 B2 | 7/2008 | Jung et al. |
| 7,421,102 B2 | 9/2008 | Wetzel et al. |
| 7,426,319 B2 | 9/2008 | Takahashi |
| 7,440,597 B2 | 10/2008 | Rowe |
| 7,450,783 B2 | 11/2008 | Talapov et al. |
| 7,460,250 B2 | 12/2008 | Keightley et al. |
| 7,474,415 B2 | 1/2009 | Lin et al. |
| 7,487,063 B2 | 2/2009 | Tubic et al. |
| 7,489,799 B2 | 2/2009 | Nilsen et al. |
| 7,495,208 B2 | 2/2009 | Czarnek et al. |
| 7,496,399 B2 | 2/2009 | Maschke |
| 7,509,861 B2 | 3/2009 | Masotti et al. |
| 7,538,869 B2 | 5/2009 | Treado et al. |
| 7,545,963 B2 | 6/2009 | Rowe |
| D597,205 S | 7/2009 | Koch |
| 7,580,590 B2 | 8/2009 | Lin et al. |
| 7,581,191 B2 | 8/2009 | Rice et al. |
| 7,587,618 B2 | 9/2009 | Inui et al. |
| 7,595,878 B2 | 9/2009 | Nelson et al. |
| 7,603,031 B1 | 10/2009 | Viaud et al. |
| D603,441 S | 11/2009 | Wada |
| 7,613,335 B2 | 11/2009 | McLennan et al. |
| 7,620,211 B2 | 11/2009 | Browne et al. |
| 7,647,085 B2 | 1/2010 | Cane et al. |
| 7,668,350 B2 | 2/2010 | Rowe |
| 7,684,589 B2 | 3/2010 | Nilsen et al. |
| 7,724,379 B2 | 5/2010 | Kawasaki et al. |
| 7,729,747 B2 | 6/2010 | Stranc et al. |
| 7,735,729 B2 | 6/2010 | Rowe |
| 7,738,032 B2 | 6/2010 | Kollias et al. |
| 7,751,594 B2 | 7/2010 | Rowe et al. |
| 7,765,487 B2 | 7/2010 | Cable |
| 7,819,311 B2 | 10/2010 | Rowe et al. |
| 7,869,641 B2 | 1/2011 | Wetzel et al. |
| 7,876,948 B2 | 1/2011 | Wetzel et al. |
| 7,881,777 B2 | 2/2011 | Docherty et al. |
| 7,894,645 B2 | 2/2011 | Barsky |
| 7,912,320 B1 | 3/2011 | Minor |
| 7,912,534 B2 | 3/2011 | Grinvald et al. |
| 7,916,834 B2 | 3/2011 | Piorek et al. |
| 7,931,149 B2 | 4/2011 | Gilad et al. |
| 7,951,395 B2 | 5/2011 | Lee et al. |
| 8,000,776 B2 | 8/2011 | Gono |
| 8,019,801 B1 | 9/2011 | Robb et al. |
| 8,026,942 B2 | 9/2011 | Payonk et al. |
| 8,071,242 B2 | 12/2011 | Rosenfeld et al. |
| 8,078,262 B2 | 12/2011 | Murphy et al. |
| 8,094,294 B2 | 1/2012 | Treado et al. |
| 8,105,233 B2 | 1/2012 | Abou El Kheir |
| D653,687 S | 2/2012 | Yu |
| 8,123,704 B2 | 2/2012 | Richards |
| 8,150,500 B2 | 4/2012 | Goldman et al. |
| 8,161,826 B1 | 4/2012 | Taylor |
| 8,165,357 B2 | 4/2012 | Rowe |
| 8,184,873 B2 | 5/2012 | Rowe et al. |
| D662,122 S | 6/2012 | Goodwin |
| D664,655 S | 7/2012 | Daniel et al. |
| 8,213,695 B2 | 7/2012 | Zouridakis |
| 8,218,862 B2 | 7/2012 | Demirli et al. |
| 8,218,873 B2 | 7/2012 | Boncyk et al. |
| 8,218,874 B2 | 7/2012 | Boncyk et al. |
| 8,224,077 B2 | 7/2012 | Boncyk et al. |
| 8,224,078 B2 | 7/2012 | Boncyk et al. |
| 8,224,079 B2 | 7/2012 | Boncyk et al. |
| 8,229,185 B2 | 7/2012 | Ennis et al. |
| 8,238,623 B2 | 8/2012 | Stephan et al. |
| 8,306,334 B2 | 11/2012 | Paschalakis et al. |
| 8,326,031 B2 | 12/2012 | Boncyk et al. |
| 8,335,351 B2 | 12/2012 | Boncyk et al. |
| 8,437,544 B2 | 5/2013 | Boncyk et al. |
| 8,457,395 B2 | 6/2013 | Boncyk et al. |
| 8,463,030 B2 | 6/2013 | Boncyk et al. |
| 8,463,031 B2 | 6/2013 | Boncyk et al. |
| 8,465,762 B2 | 6/2013 | Lee et al. |
| 8,467,600 B2 | 6/2013 | Boncyk et al. |
| 8,467,602 B2 | 6/2013 | Boncyk et al. |
| 8,478,036 B2 | 7/2013 | Boncyk et al. |
| 8,478,037 B2 | 7/2013 | Boncyk et al. |
| 8,480,641 B2 | 7/2013 | Jacobs |
| 8,488,880 B2 | 7/2013 | Boncyk et al. |
| 8,494,264 B2 | 7/2013 | Boncyk et al. |
| 8,498,460 B2 | 7/2013 | Patwardhan |
| 8,520,942 B2 | 8/2013 | Boncyk et al. |
| 8,533,879 B1 | 9/2013 | Taylor |
| 8,548,245 B2 | 10/2013 | Boncyk et al. |
| 8,548,278 B2 | 10/2013 | Boncyk et al. |
| 8,582,817 B2 | 11/2013 | Boncyk et al. |
| 8,588,476 B1 | 11/2013 | Spicola, Jr. |
| 8,588,527 B2 | 11/2013 | Boncyk et al. |
| D697,210 S | 1/2014 | Delaney et al. |
| 8,638,986 B2 | 1/2014 | Jiang et al. |
| 8,661,915 B2 | 3/2014 | Taylor |
| 8,712,193 B2 | 4/2014 | Boncyk et al. |
| 8,718,410 B2 | 5/2014 | Boncyk et al. |
| 8,734,342 B2 | 5/2014 | Cable |
| 8,755,053 B2 | 6/2014 | Fright et al. |
| 8,768,052 B2 | 7/2014 | Kawano |
| 8,773,508 B2 | 7/2014 | Daniel et al. |
| 8,774,463 B2 | 7/2014 | Boncyk et al. |
| 8,787,621 B2 | 7/2014 | Spicola, Sr. et al. |
| 8,787,630 B2 | 7/2014 | Rowe |
| 8,795,169 B2 | 8/2014 | Cosentino et al. |
| 8,798,368 B2 | 8/2014 | Boncyk et al. |
| 8,800,386 B2 | 8/2014 | Taylor |
| 8,814,841 B2 | 8/2014 | Hartwell |
| 8,824,738 B2 | 9/2014 | Boncyk et al. |
| 8,837,868 B2 | 9/2014 | Boncyk et al. |
| 8,842,941 B2 | 9/2014 | Boncyk et al. |
| 8,849,380 B2 | 9/2014 | Patwardhan |
| D714,940 S | 10/2014 | Kim |
| 8,855,423 B2 | 10/2014 | Boncyk et al. |
| 8,861,859 B2 | 10/2014 | Boncyk et al. |
| 8,867,839 B2 | 10/2014 | Boncyk et al. |
| 8,873,891 B2 | 10/2014 | Boncyk et al. |
| 8,875,331 B2 | 11/2014 | Taylor |
| 8,885,983 B2 | 11/2014 | Boncyk et al. |
| 8,892,190 B2 | 11/2014 | Docherty et al. |
| 8,904,876 B2 | 12/2014 | Taylor et al. |
| 8,913,800 B2 | 12/2014 | Rowe |
| 8,923,563 B2 | 12/2014 | Boncyk et al. |
| D720,864 S | 1/2015 | Behar et al. |
| 8,938,096 B2 | 1/2015 | Boncyk et al. |
| 8,939,918 B2 | 1/2015 | Richards |
| 8,948,459 B2 | 2/2015 | Boncyk et al. |
| 8,948,460 B2 | 2/2015 | Boncyk et al. |
| D724,216 S | 3/2015 | Gant et al. |
| 8,997,588 B2 | 4/2015 | Taylor |

(56) References Cited

U.S. PATENT DOCUMENTS

| | | |
|---|---|---|
| 9,014,513 B2 | 4/2015 | Boncyk et al. |
| 9,014,514 B2 | 4/2015 | Boncyk et al. |
| 9,014,515 B2 | 4/2015 | Boncyk, V et al. |
| 9,020,305 B2 | 4/2015 | Boncyk et al. |
| 9,025,813 B2 | 5/2015 | Boncyk et al. |
| 9,025,814 B2 | 5/2015 | Boncyk et al. |
| 9,031,278 B2 | 5/2015 | Boncyk et al. |
| 9,036,947 B2 | 5/2015 | Boncyk et al. |
| 9,036,948 B2 | 5/2015 | Boncyk et al. |
| 9,041,810 B2 | 5/2015 | Ecker et al. |
| D735,879 S | 8/2015 | Behar et al. |
| 9,110,925 B2 | 8/2015 | Boncyk et al. |
| 9,116,920 B2 | 8/2015 | Boncyk et al. |
| 9,135,355 B2 | 9/2015 | Boncyk et al. |
| 9,141,714 B2 | 9/2015 | Boncyk et al. |
| 9,148,562 B2 | 9/2015 | Boncyk et al. |
| D740,945 S | 10/2015 | Booth |
| 9,154,694 B2 | 10/2015 | Boncyk et al. |
| 9,154,695 B2 | 10/2015 | Boncyk et al. |
| 9,167,800 B2 | 10/2015 | Spicola, Jr. |
| 9,179,844 B2 * | 11/2015 | Fright .................. H05K 999/99 |
| 9,186,053 B2 | 11/2015 | Viola |
| 9,196,067 B1 | 11/2015 | Freed et al. |
| 9,224,205 B2 | 12/2015 | Tsin et al. |
| 9,235,600 B2 | 1/2016 | Boncyk et al. |
| 9,244,943 B2 | 1/2016 | Boncyk et al. |
| 9,262,440 B2 | 2/2016 | Boncyk et al. |
| 9,268,197 B1 | 2/2016 | Digregorio et al. |
| 9,285,323 B2 | 3/2016 | Burg et al. |
| 9,288,271 B2 | 3/2016 | Boncyk et al. |
| 9,311,520 B2 | 4/2016 | Burg et al. |
| 9,311,540 B2 | 4/2016 | Ecker et al. |
| 9,311,552 B2 | 4/2016 | Boncyk et al. |
| 9,311,553 B2 | 4/2016 | Boncyk et al. |
| 9,311,554 B2 | 4/2016 | Boncyk et al. |
| 9,317,769 B2 | 4/2016 | Boncyk et al. |
| 9,324,004 B2 | 4/2016 | Boncyk et al. |
| 9,330,326 B2 | 5/2016 | Boncyk et al. |
| 9,330,327 B2 | 5/2016 | Boncyk et al. |
| 9,330,328 B2 | 5/2016 | Boncyk et al. |
| 9,330,453 B2 | 5/2016 | Soldatitsch et al. |
| 9,342,748 B2 | 5/2016 | Boncyk et al. |
| D758,608 S | 6/2016 | Behar et al. |
| 9,377,295 B2 | 6/2016 | Fright et al. |
| 9,395,234 B2 | 7/2016 | Cosentino et al. |
| 9,399,676 B2 | 7/2016 | Schurpf et al. |
| 9,438,775 B2 | 9/2016 | Powers |
| 9,451,928 B2 | 9/2016 | Falco et al. |
| 9,525,867 B2 | 12/2016 | Thomas et al. |
| 9,528,941 B2 | 12/2016 | Burg et al. |
| 9,607,380 B2 | 3/2017 | Burg et al. |
| D783,838 S | 4/2017 | Zhao et al. |
| 9,690,904 B1 | 6/2017 | Zizi |
| 9,808,206 B1 | 11/2017 | Zhao et al. |
| 9,818,193 B2 | 11/2017 | Smart |
| 9,861,285 B2 * | 1/2018 | Fright .................. H05K 999/99 |
| 9,863,811 B2 | 1/2018 | Burg |
| 9,955,910 B2 | 5/2018 | Fright et al. |
| 9,972,077 B2 | 5/2018 | Adiri et al. |
| 9,996,923 B2 | 6/2018 | Thomas |
| 10,013,527 B2 | 7/2018 | Fairbairn et al. |
| D827,827 S | 9/2018 | Canfield et al. |
| 10,068,329 B2 | 9/2018 | Adiri et al. |
| D831,197 S | 10/2018 | Scruggs et al. |
| 10,117,617 B2 | 11/2018 | Cantu et al. |
| 10,130,260 B2 | 11/2018 | Patwardhan |
| 10,143,425 B1 | 12/2018 | Zhao et al. |
| D837,388 S | 1/2019 | Dacosta et al. |
| 10,267,743 B2 | 4/2019 | Burg et al. |
| 10,307,382 B2 | 6/2019 | Jung et al. |
| 10,362,984 B2 | 7/2019 | Adiri et al. |
| 10,368,795 B2 | 8/2019 | Patwardhan |
| 10,559,081 B2 | 2/2020 | Omer et al. |
| RE47,921 E | 3/2020 | Patwardhan |
| D877,931 S | 3/2020 | Dacosta et al. |
| 10,614,623 B2 | 4/2020 | D'alessandro |
| 10,617,305 B2 | 4/2020 | Patwardhan et al. |
| 10,652,520 B2 | 5/2020 | Otto et al. |
| 10,674,953 B2 | 6/2020 | Baker et al. |
| 10,692,214 B2 | 6/2020 | Bisker |
| 10,702,160 B2 | 7/2020 | Patwardhan |
| 10,775,647 B2 | 9/2020 | Joy et al. |
| 10,777,317 B2 | 9/2020 | Fairbairn et al. |
| D898,921 S | 10/2020 | Dacosta et al. |
| D899,604 S | 10/2020 | Dacosta et al. |
| D903,863 S | 12/2020 | Dacosta et al. |
| 10,874,302 B2 * | 12/2020 | Fright .................... A61B 5/445 |
| 11,116,407 B2 | 9/2021 | Dickie et al. |
| 11,134,848 B2 | 10/2021 | Bala et al. |
| 11,250,945 B2 | 2/2022 | Fairbairn et al. |
| 2002/0054297 A1 | 5/2002 | Lee et al. |
| 2002/0149585 A1 | 10/2002 | Kacyra et al. |
| 2002/0197600 A1 | 12/2002 | Maione et al. |
| 2003/0004405 A1 | 1/2003 | Townsend et al. |
| 2003/0006770 A1 | 1/2003 | Smith |
| 2003/0031383 A1 | 2/2003 | Gooch |
| 2003/0036751 A1 | 2/2003 | Anderson et al. |
| 2003/0085908 A1 | 5/2003 | Luby |
| 2003/0164841 A1 | 9/2003 | Myers |
| 2003/0164875 A1 | 9/2003 | Myers |
| 2003/0229514 A2 | 12/2003 | Brown |
| 2003/0231793 A1 | 12/2003 | Crampton |
| 2004/0013292 A1 | 1/2004 | Raunig |
| 2004/0014165 A1 | 1/2004 | Keidar et al. |
| 2004/0059199 A1 | 3/2004 | Thomas et al. |
| 2004/0080497 A1 | 4/2004 | Enmei |
| 2004/0117343 A1 | 6/2004 | Johnson |
| 2004/0136579 A1 | 7/2004 | Gutenev |
| 2004/0146290 A1 | 7/2004 | Kollias et al. |
| 2004/0201694 A1 | 10/2004 | Gartstein et al. |
| 2004/0225222 A1 | 11/2004 | Zeng et al. |
| 2004/0264749 A1 | 12/2004 | Skladnev et al. |
| 2005/0012817 A1 | 1/2005 | Hampapur et al. |
| 2005/0027567 A1 | 2/2005 | Taha |
| 2005/0033142 A1 | 2/2005 | Madden et al. |
| 2005/0084176 A1 | 4/2005 | Talapov et al. |
| 2005/0094262 A1 | 5/2005 | Spediacci et al. |
| 2005/0111757 A1 | 5/2005 | Brackett et al. |
| 2005/0154276 A1 | 7/2005 | Barducci et al. |
| 2005/0190988 A1 | 9/2005 | Feron |
| 2005/0237384 A1 | 10/2005 | Jess et al. |
| 2005/0259281 A1 | 11/2005 | Boust |
| 2005/0273011 A1 | 12/2005 | Hattery et al. |
| 2005/0273267 A1 | 12/2005 | Maione |
| 2006/0008178 A1 | 1/2006 | Seeger et al. |
| 2006/0012802 A1 | 1/2006 | Shirley |
| 2006/0036135 A1 | 2/2006 | Kern |
| 2006/0036156 A1 | 2/2006 | Lachaine et al. |
| 2006/0044546 A1 | 3/2006 | Lewin et al. |
| 2006/0055943 A1 | 3/2006 | Kawasaki et al. |
| 2006/0058665 A1 | 3/2006 | Chapman |
| 2006/0072122 A1 | 4/2006 | Hu et al. |
| 2006/0073132 A1 | 4/2006 | Congote |
| 2006/0089553 A1 | 4/2006 | Cotton |
| 2006/0098876 A1 | 5/2006 | Buscema |
| 2006/0135953 A1 | 6/2006 | Kania et al. |
| 2006/0151601 A1 | 7/2006 | Rosenfeld |
| 2006/0159341 A1 | 7/2006 | Pekar et al. |
| 2006/0204072 A1 | 9/2006 | Wetzel et al. |
| 2006/0210132 A1 | 9/2006 | Christiansen et al. |
| 2006/0222263 A1 | 10/2006 | Carlson |
| 2006/0268148 A1 | 11/2006 | Kollias et al. |
| 2006/0269125 A1 | 11/2006 | Kalevo et al. |
| 2006/0293613 A1 | 12/2006 | Fatehi et al. |
| 2007/0065009 A1 | 3/2007 | Ni et al. |
| 2007/0097381 A1 | 5/2007 | Tobiason et al. |
| 2007/0125390 A1 | 6/2007 | Afriat et al. |
| 2007/0129602 A1 | 6/2007 | Bettesh et al. |
| 2007/0229850 A1 | 10/2007 | Herber |
| 2007/0273894 A1 | 11/2007 | Johnson |
| 2007/0276195 A1 | 11/2007 | Xu et al. |
| 2007/0276309 A1 | 11/2007 | Xu et al. |
| 2008/0006282 A1 | 1/2008 | Sukovic |
| 2008/0021329 A1 | 1/2008 | Wood et al. |

(56) References Cited

U.S. PATENT DOCUMENTS

| | | |
|---|---|---|
| 2008/0045807 A1 | 2/2008 | Psota et al. |
| 2008/0088704 A1 | 4/2008 | Wendelken et al. |
| 2008/0098322 A1 | 4/2008 | Champion et al. |
| 2008/0126478 A1 | 5/2008 | Ferguson et al. |
| 2008/0165357 A1 | 7/2008 | Stern |
| 2008/0232679 A1 | 9/2008 | Hahn |
| 2008/0246759 A1 | 10/2008 | Summers |
| 2008/0275315 A1 | 11/2008 | Oka et al. |
| 2008/0285056 A1 | 11/2008 | Blayvas |
| 2008/0312642 A1 | 12/2008 | Kania et al. |
| 2008/0312643 A1 | 12/2008 | Kania et al. |
| 2009/0116712 A1 | 5/2009 | Al-Moosawi et al. |
| 2009/0118720 A1 | 5/2009 | Black et al. |
| 2009/0221874 A1 | 9/2009 | Vinther |
| 2009/0225333 A1 | 9/2009 | Bendall |
| 2009/0234313 A1 | 9/2009 | Mullejeans et al. |
| 2010/0004564 A1 | 1/2010 | Jendle |
| 2010/0020164 A1 | 1/2010 | Perrault |
| 2010/0091104 A1 | 4/2010 | Sprigle et al. |
| 2010/0111387 A1 | 5/2010 | Christiansen, II et al. |
| 2010/0113940 A1 | 5/2010 | Sen et al. |
| 2010/0121201 A1 | 5/2010 | Papaioannou |
| 2010/0149551 A1 | 6/2010 | Malinkevich |
| 2010/0156921 A1 | 6/2010 | McLennan et al. |
| 2010/0191126 A1 | 7/2010 | Al-Moosawi et al. |
| 2010/0278312 A1 | 11/2010 | Ortiz |
| 2011/0102550 A1 | 5/2011 | Daniel et al. |
| 2011/0125028 A1 | 5/2011 | Wood et al. |
| 2011/0190637 A1 | 8/2011 | Knobel et al. |
| 2012/0035469 A1 | 2/2012 | Whelan et al. |
| 2012/0059266 A1 | 3/2012 | Davis et al. |
| 2012/0078088 A1 | 3/2012 | Whitestone et al. |
| 2012/0078113 A1 | 3/2012 | Whitestone et al. |
| 2012/0253200 A1 | 10/2012 | Stolka et al. |
| 2012/0265236 A1 | 10/2012 | Wesselmann |
| 2012/0275668 A1 | 11/2012 | Chou et al. |
| 2013/0051651 A1 | 2/2013 | Leary et al. |
| 2013/0162796 A1 | 6/2013 | Bharara et al. |
| 2013/0335545 A1 | 12/2013 | Darling |
| 2014/0048687 A1 | 2/2014 | Drzymala et al. |
| 2014/0088402 A1 | 3/2014 | Xu |
| 2014/0354830 A1 | 12/2014 | Schafer et al. |
| 2015/0077517 A1 | 3/2015 | Powers |
| 2015/0089994 A1 | 4/2015 | Richards |
| 2015/0142462 A1 | 5/2015 | Vaidya et al. |
| 2015/0150457 A1 | 6/2015 | Wu et al. |
| 2015/0214993 A1 | 7/2015 | Huang |
| 2015/0250416 A1 | 9/2015 | LaPlante et al. |
| 2015/0265236 A1 | 9/2015 | Garner et al. |
| 2015/0270734 A1 | 9/2015 | Davison et al. |
| 2016/0100790 A1 | 4/2016 | Cantu et al. |
| 2016/0157725 A1 | 6/2016 | Munoz |
| 2016/0206205 A1 | 7/2016 | Wu et al. |
| 2016/0259992 A1 | 9/2016 | Knodt et al. |
| 2016/0261133 A1 | 9/2016 | Wang |
| 2016/0262659 A1 | 9/2016 | Fright et al. |
| 2016/0275681 A1 | 9/2016 | D'alessandro |
| 2016/0284084 A1 | 9/2016 | Gurcan et al. |
| 2016/0338594 A1 | 11/2016 | Spahn et al. |
| 2017/0076446 A1 | 3/2017 | Pedersen et al. |
| 2017/0079577 A1 | 3/2017 | Fright et al. |
| 2017/0084024 A1 | 3/2017 | Gurevich |
| 2017/0085764 A1 | 3/2017 | Kim et al. |
| 2017/0086940 A1 | 3/2017 | Nakamura |
| 2017/0127196 A1 | 5/2017 | Blum et al. |
| 2017/0236273 A1 | 8/2017 | Kim et al. |
| 2017/0258340 A1 | 9/2017 | Przybyszewski et al. |
| 2017/0262985 A1 | 9/2017 | Finn et al. |
| 2017/0303790 A1 | 10/2017 | Bala et al. |
| 2017/0303844 A1 | 10/2017 | Baker et al. |
| 2018/0132726 A1 | 5/2018 | Dickie et al. |
| 2018/0214071 A1 | 8/2018 | Fright et al. |
| 2018/0252585 A1 | 9/2018 | Burg |
| 2018/0279943 A1 | 10/2018 | Budman et al. |
| 2018/0296092 A1 | 10/2018 | Hassan et al. |
| 2018/0303413 A1 | 10/2018 | Hassan et al. |
| 2018/0322647 A1 | 11/2018 | Harrington et al. |
| 2018/0336720 A1 | 11/2018 | Larkins et al. |
| 2019/0133513 A1 | 5/2019 | Patwardhan |
| 2019/0240166 A1 | 8/2019 | Jung et al. |
| 2019/0290187 A1 | 9/2019 | Ariri et al. |
| 2019/0298183 A1 | 10/2019 | Burg et al. |
| 2019/0298252 A1 | 10/2019 | Patwardhan |
| 2019/0307337 A1 | 10/2019 | Little et al. |
| 2019/0307400 A1 | 10/2019 | Zhao et al. |
| 2019/0310203 A1 | 10/2019 | Burg et al. |
| 2019/0336003 A1 | 11/2019 | Patwardhan |
| 2019/0350535 A1 | 11/2019 | Zhao et al. |
| 2019/0369418 A1 | 12/2019 | Joy et al. |
| 2020/0014910 A1 | 1/2020 | Larkins |
| 2020/0121245 A1 | 4/2020 | Barclay et al. |
| 2020/0126226 A1 | 4/2020 | Adiri et al. |
| 2020/0126227 A1 | 4/2020 | Adiri et al. |
| 2020/0196962 A1 | 6/2020 | Zhao et al. |
| 2020/0209214 A1 | 7/2020 | Zohar et al. |
| 2020/0211193 A1 | 7/2020 | Adiri et al. |
| 2020/0211228 A1 | 7/2020 | Adiri et al. |
| 2020/0211682 A1 | 7/2020 | Zohar et al. |
| 2020/0211693 A1 | 7/2020 | Adiri et al. |
| 2020/0211697 A1 | 7/2020 | Adiri et al. |
| 2020/0225166 A1 | 7/2020 | Burg et al. |
| 2020/0234444 A1 | 7/2020 | Budman et al. |
| 2020/0286600 A1 | 9/2020 | De Brouwer et al. |
| 2020/0297213 A1 | 9/2020 | Patwardhan |
| 2020/0359971 A1 | 11/2020 | Zhao et al. |
| 2020/0364862 A1 | 11/2020 | Dacosta et al. |
| 2020/0383631 A1 | 12/2020 | Canfield et al. |
| 2021/0000387 A1 | 1/2021 | Zizi |
| 2021/0004995 A1 | 1/2021 | Burg et al. |
| 2021/0219907 A1 | 7/2021 | Fright et al. |
| 2021/0386295 A1 | 12/2021 | Dickie et al. |
| 2022/0215538 A1 | 7/2022 | Robinson et al. |
| 2022/0270746 A1 | 8/2022 | Fairbairn et al. |

FOREIGN PATENT DOCUMENTS

| | | |
|---|---|---|
| DE | 2642841 | 3/1978 |
| DE | 3420588 | 12/1984 |
| DE | 4120074 | 1/1992 |
| EP | 355221 | 2/1990 |
| EP | 552526 | 7/1993 |
| EP | 650694 | 5/1995 |
| EP | 1210906 | 6/2002 |
| EP | 1248237 | 10/2002 |
| EP | 1351036 | 10/2003 |
| EP | 1303267 | 4/2004 |
| EP | 1584405 | 10/2005 |
| EP | 1611543 | 1/2006 |
| EP | 1467706 | 3/2007 |
| EP | 1946567 | 7/2008 |
| EP | 119660 | 5/2009 |
| EP | 2272047 | 3/2012 |
| EP | 2883037 | 6/2015 |
| EP | 3114462 | 1/2017 |
| EP | 3143378 | 3/2017 |
| EP | 3160327 | 5/2017 |
| EP | 2750673 | 8/2017 |
| EP | 3251332 | 12/2017 |
| EP | 3270770 | 1/2018 |
| EP | 3286695 | 2/2018 |
| EP | 3364859 | 8/2018 |
| EP | 3365057 | 8/2018 |
| EP | 3371779 | 9/2018 |
| EP | 3371780 | 9/2018 |
| EP | 3381015 | 11/2019 |
| EP | 3586195 | 1/2020 |
| EP | 3589187 | 1/2020 |
| EP | 3602501 | 2/2020 |
| EP | 3555856 | 4/2020 |
| EP | 3655924 | 5/2020 |
| EP | 3371781 | 9/2020 |
| EP | 3707670 | 9/2020 |
| EP | 4183328 | 5/2023 |
| ES | 2384086 | 6/2012 |

(56) References Cited

FOREIGN PATENT DOCUMENTS

| | | |
|---|---|---|
| FR | 2570206 | 3/1986 |
| GB | 2458927 | 11/2012 |
| GB | 2544263 | 5/2017 |
| GB | 2544460 | 5/2017 |
| GB | 2544725 | 5/2017 |
| GB | 2545394 | 6/2017 |
| GB | 2557633 | 6/2018 |
| GB | 2557928 | 7/2018 |
| GB | 2559977 | 8/2018 |
| GB | 2559978 | 8/2018 |
| IN | Z293713 | 9/1997 |
| JP | 2011516849 | 5/2011 |
| JP | 5467404 | 4/2014 |
| NZ | 588740 | 7/2012 |
| WO | WO2000003210 | 1/2000 |
| WO | WO2000030337 | 5/2000 |
| WO | WO2002001143 | 1/2002 |
| WO | WO2002065069 | 8/2002 |
| WO | WO2002093450 | 11/2002 |
| WO | WO2004092874 | 10/2004 |
| WO | WO2004095372 | 11/2004 |
| WO | WO2005033620 | 4/2005 |
| WO | WO2006078902 | 7/2006 |
| WO | WO2007029038 | 3/2007 |
| WO | WO2007043899 | 4/2007 |
| WO | WO2007059780 | 5/2007 |
| WO | WO2008033010 | 3/2008 |
| WO | WO2008039539 | 4/2008 |
| WO | WO2008048424 | 4/2008 |
| WO | WO2008057056 | 5/2008 |
| WO | WO2008071414 | 6/2008 |
| WO | WO2008080385 | 7/2008 |
| WO | WO2009046218 | 4/2009 |
| WO | WO2009122200 | 10/2009 |
| WO | WO2010048960 | 5/2010 |
| WO | WO2012146720 | 11/2012 |
| WO | WO2016069463 | 5/2016 |
| WO | WO2016199134 | 12/2016 |
| WO | WO2017077276 | 5/2017 |
| WO | WO2017077277 | 5/2017 |
| WO | WO2017077279 | 5/2017 |
| WO | WO2017089826 | 6/2017 |
| WO | WO2018109453 | 6/2018 |
| WO | WO2018109479 | 6/2018 |
| WO | WO2018154271 | 8/2018 |
| WO | WO2018154272 | 8/2018 |
| WO | WO2018185560 | 10/2018 |
| WO | WO2019239106 | 12/2019 |
| WO | WO2019239147 | 12/2019 |
| WO | WO2020014779 | 1/2020 |
| WO | WO2020141346 | 7/2020 |
| WO | WO2020251938 | 12/2020 |

OTHER PUBLICATIONS

Kumar et al., "Wound Image Analysis Classifier for Efficient Tracking of Wound Healing Status," Signal & Image Processing: An International Journal (SIPIJ), vol. 5, No. 2, Apr. 2014, pp. 15-27.
Mashburn et al., "Enabling user-guided segmentation and tracking of surface-labeled cells in time-lapse image sets of living tissues," Cytometry A., NIH Public Access, May 1, 2013, pp. 1-17.
Plaza et al., "Minimizing Manual Image Segmentation Turn-Around Time for Neuronal Reconstruction by Embracing Uncertainty," PLOS ONE, vol. 7, Issue 9, Sep. 2012, pp. 1-14.
Non-Final Office Action dated Nov. 24, 2021, U.S. Appl. No. 16/500,785, 34 pages.
Non-Final Office Action dated Oct. 24, 2022, U.S. Appl. No. 17/398,883, 18 pages.
Afromowitz, et al., "Multispectral Imaging of Burn Wounds: A New Clinical Instrument for Evaluating Burn Depth", IEEE Transactions on Biomedical Engineering, vol. 35, No. 10, pp. 842-850; Oct. 1988.
Ahn et al., "Advances in Wound Photography and Assessment Methods," Advances in Skin & Wound Care, Feb. 2008, pp. 85-93.
Ahroni, JH et al., "Reliability of computerized wound surface area determinations" Wounds: A Compendium of Clinical Research and Practice, No. 4, (1992) 133-137.
Anderson, R., et al. "The Optics of Human Skin", The Journal of Investigative Dermatology, vol. 77, No. 1, pp. 13-19; Jul. 1981.
Armstrong, DG et al "Diabetic foot ulcers: prevention, diagnosis and classification" Am Fam Physician Mar. 15, 1998; 57 (6) : 1325-32, 1337-8.
Bale, S, Harding K, Leaper D. An Introduction to Wounds. Emap Healthcare Ltd 2000.
Beaumont, E et al "RN Technology Scorecard: Wound Care Science at the Crossroads" American Journal of Nursing Dec. 1998 98(12):16-18, 20-21.
Bergstrom, N, Bennett MA, Carlson CE. Treatment of Pressure Ulcers: Clinical Practice Guideline No. 15. Rockville, MD: U.S. Department of Health and Human Services. Public Health Service, Agency for Health Care Policy and Research 1994: 95-0652: [O].
Berriss 1997: Automatic Quantitative Analysis of Healing Skin Wounds using Colour Digital Image Processing: William Paul Berriss, Stephen John Sangwine [E].
Binder, et al., "Application of an artificial neural network in epiluminescence microscopy pattern analysis of pigmented skin lesions: a pilot study", British Journal of Dermatology 130; pp. 460-465; 1994.
Bland, JM et al. "Measurement error and correlation coefficients" BMJ Jul. 6, 1996; 313 (7048) :41-2.
Bland, JM et al. "Measurement error" BMJ Jun. 29, 1996; 312 (7047) :1654.
Bohannon Richard; Barbara A Pfaller Documentation of Wound Surface Area from Tracings of Wound Perimeters [E].
Bolton, L., "Re Measuring Wound Length, Width, and Area: Which Technique?" Letters, Advances in Skin & Wound Care, pp. 450-452, vol. 21, No. 10.
Bostock, et al, Toward a neural network based system for skin cancer diagnosis; IEEE Conference on Artificial neural Networks, ISBN: 0-85296-573-7, pp. 215-219, May 1993.
BPG2005: Assessment and Management of Foot Ulcers for People with Diabetes:Nursing Best Practice Guidelines, Toronto, Ontario [E], Mar. 2013.
Briers, J.D., "Laser speckle contrast imaging for measuring blood flow," Optica Applicata, 2007, pp. 139-152, vol. XXXVII, No. 1-2.
Briggs Corporation: Managed care making photo documentation a wound care standard. Wound care solutions product catalog 1997.
Brown, G "Reporting outcomes for Stage IV pressure ulcer healing: a proposal" Adv Skin Wound Care (2000)13:277-83.
Callieri 2003: Callieri M, Cignoni P, Pingi P, Scopigno R. Derma: Monitoring the evolution of skin lesions with a 3D system, VMV 2003. 8th International Fall Workshop, Vision, Modeling, and Visualization 2003, Nov. 19-21, 2003, Munich, Germany [E].
Campana: XML-based synchronization of mobile medical devices [E], 2002, 2 Pages.
Cardinal et al., "Early healing rates and wound area measurements are reliable predictors of later complete wound closure," Wound Rep. Reg., 2008, pp. 19-22, vol. 16.
Cardinal et al., "Wound shape geometry measurements correlate to eventual wound healing," Wound Rep. Reg., 2009, pp. 173-178, vol. 17.
Cascinelli, N., et al. "Results obtained by using a computerized image analysis system designed as an aid to diagnosis of cutaneous melanoma", Melanoma Research, vol. 2, pp. 163-170, 1992.
Cleator et al., "Mobile wound care: Transforming care through technology," Rehab & Community Care Medicine, Winter 2008, pp. 14-15.
Collins, C et al "The Role of Ultrasound in Lower Extremity Wound Management" International Journal of Lower Extremity Wounds (2002) 1: 229-235.
Daubechies, I., "The Wavelet Transform, Time-Frequency Localization and Signal Analysis", IEEE Trans Inform Theory, vol. 36, No. 5, pp. 961-1005; Sep. 1990.
De Vet, HC et al "Current challenges in clinimetrics" J Clin Epidemiol Dec. 2003; 56 (12) : 1137-41.

(56) References Cited

OTHER PUBLICATIONS

De Vet, H C., et al., "When to use agreement versus reliability measures", J Clin Eoidemiol 59 (10), (Oct. 2006), 1033-9.
Debray, M., Couturier P. Greuillet F, Hohn C, Banerjee S, Gavazzi G, Franco A. "A preliminary study of the feasibility of wound telecare for the elderly." Journal of Telemedicine & Telecare 2001: 7(6): 353-8. [A].
Duckworth et al., "A Clinically Affordable Non-Contact Wound Measurement Device," 2007, pp. 1-3.
Duff, et al. (2003), Loftus Hills A, Morrell C 2000 Clinical. Guidelines for the management of venous leg ulcers: Implementation Guide. Royal College of Nursing: 2000: 001 (213): 1-48. [E].
Ercal, F., "Detection of Skin Tumor Boundaries in Color Images", IEEE Transactions of Medical Imaging, vol. 12, No. 3, pp. 624-627, Sep. 1993.
Ercal, F., et al. "Neural Network Diagnosis of Malignant Melanoma From Color Images", IEEE Transactions of Biomedical Engineering, vol. 41, No. 9, pp. 837-845, Sep. 1994.
Ferrell, B "Pressure ulcers. Assessment of healing" Clin Geriatr Med (1997) 13:575-87.
Fette, A.M., "A clinimetric analysis of wound measurement tools," World Wide Wounds, 2006, [retrieved on Jul. 26, 2006]. Retrieved from the Internet: < URL: http://www.worldwidewounds.com/2006/January/Fette/Clinimetric-Ana . . . >, 6 pages.
Fitzpatrick et al., "Evaluating patient-based outcome measures for use in clinical trials," Health Technology Assessment, 1998, vol. 2, No. 14, 86 pages.
Flahr et al., "Clinimetrics and Wound Science," Wound Care Canada, 2005, pp. 18-19, 48, vol. 3, No. 2.
Flanagan, M. "Improving accuracy of wound measurement in clinical practice" Ostomy Wound Manage Oct. 2003, 49(10):28-40.
Flanagan, M., "Wound measurement: can it help us to monitor progression to healing?" JWound Care May 2003, 12(5):189-94.
Gethin et al., "Wound Measurement: the contribution to practice," EWMA Journal, 2007, pp. 26-28, vol. 7, No. 1.
Gilman, T "Wound outcomes: the utility of surface measures" Int J Low Extrem Wounds Sep. 2004; 3 (3) : 125-32.
Goldman, RJ "The patientcom, 1 year later" AdvSkin Wound Care Nov.-Dec. 2002; 15 (6) :254, 256.
Goldman, RJ et al "More than one way to measure a wound: An overview of tools and techniques" AdvSkin Wound Care (2002) 15:236-45.
Golston, et al. "Automatic Detection of Irregular Borders in Melanoma and Other Skin Tumors", Computerized Medical Imaging and Graphics, vol. 16, No. 3, pp. 199-203, 1992.
Graaf, R., et al. "Optical properties of human dermis in vitro and in vivo", Applied Optics, vol. 32, No. 4, pp. 435-447, Feb. 1, 1993.
Greene, A., "Computer image analysis in the diagnosis of melanoma", Journal of the American Academy of Dermatology: vol. 31, No. 6, pp. 958-964, 1994.
Griffin, JW et al. "A comparison of photographic and transparency-based methods for measuring wound surface area" Phys Ther Feb. 1993; 73 (2) :117-22.
Haghpanah et al., "Reliability of Electronic Versus Manual Wound Measurement Techniques," Arch Phys Med Rehabil, Oct. 2006, pp. 1396-1402, vol. 87.
Hansen 1997: Wound Status Evaluation Using Color Image Processing Gary: L. Hansen, Ephraim M. Sparrow, Jaydeep Y. Kokate, Keith J. Leland, and Paul A. Iaizzo [E].
Hayes 2003:Hayes S, Dodds, S. Digital photography in wound care. Nursing Times 2003:9(42):48-9. [A].
Herbin, et al, Color Quantitation Through Image Processing in Dermatology; IEEE Transaction on Medical Imaging, vol. 9, Issue 3, pp. 262-269, Sep. 1990.
Hibbs, P "The economics of pressure ulcer prevention" Decubitus Aug. 1988; 1 (3) :32-8.
Houghton 2000: Houghton PE, Kincaid CB, Campbell KE, Woodbury MG, Keast DH. Photographic assessment of the appearance of chronic pressure and leg ulcers. Ostomy Wound management 2000: 46(4): 20-6, 28-30. [A].

HSA Global, "Mobile Wound Care", Marketing material (2009).
Huang, C., et al. "Border irregularity: atypical moles versus melanoma", Eur J Dermatol, vol. 6, pp. 270-273, Jun. 1996.
Iakovou, D et al., "Integrated sensors for robotic laser welding," Proceedings of the Third International WLT-Conference on Lasers in Manufacturing, Jun. 2005, pp. 1-6.
International Search Report and Written Opinion for International Application No. PCT/US2004/028445 filed Sep. 1, 2004.
International Search Report and Written Opinion dated Jan. 23, 2019, International Application No. PCT/IB2018/000447, 20 pages.
International Search Report and Written Opinion dated Jul. 2, 2019, International Application No. PCT/IB2018/001572, 17 pages.
International Search Report and Written Opinion dated Mar. 1, 2007, International Application No. PCT/NZ2006/000262, 12 pages.
Johnson, JD (1995) Using ulcer surface area and volume to document wound size, J Am Podiatr Med Assoc 85(2), (Feb. 1995), 91-5.
Jones, et al, An Instrument to Measure the Dimension of Skin Wounds; IEEE Transaction on Biomedical Engineering, ISSN: 0018-9294; vol. 42, Issue 5, pp. 464-470, May 1995.
Jones, TD "Improving the Precision of Leg Ulcer Area Measurement with Active Contour Models", PhD Thesis (1999) http://www.comp.glam.ac.uklpages/staff/tjones/ThesisOL/Title. Htm.
Jones, TD et al. "An active contour model for measuring the area of leg ulcers" IEEE Trans Med Imaging Dec. 2000, 19(12):1202-10.
Kecelj-Leskovec et al., "Measurement of venous leg ulcers with a laser-based three-dimensional method: Comparison to computer planimetry with photography," Wound Rep Reg, 2007, pp. 767-771, vol. 15.
Kenet, R., et al. "Clinical Diagnosis of Pigmented Lesions Using Digital Epiluminescence Microscopy", Arch Dermatol, vol. 129, pp. 157-174; Feb. 1993.
Khashram et al., "Effect ofTNP on the microbiology of venous leg ulcers: a pilot study," J Wound Care, Apr. 2009, pp. 164-167, vol. 18, No. 4.
Kloth, LC et al "A Randomized Controlled Clinical Trial to Evaluate the Effects of Noncontact Normothermic Wound Therapy on Chronic Full-thickness Pressure Ulcers" Advances in Skin & Wound Care Nov./Dec. 2002, 15(6):270-276.
Korber et al., "Three-dimensional documentation of wound healing: First results of a new objective method for measurement," JDDG, Oct. 2006, (Band 4), pp. 848-854.
Koren, et al, Interactive Wavelet Processing and Techniques Applied to Digital Mammography; IEEE Conference Proceedings, ISBN: 0-7803-3192-3; vol. 3, pp. 1415-1418, May 1996.
Kovesi, P., "Image Features From Phase Congruency", University of Western Australia, pp. 1-30; Technical Report 9/4, Revised Jun. 1995.
Krouskop, TA et al "A noncontact wound measurement system" J Rehabil Res Dev May-Jun. 2002, 39(3):337-45.
Kundin 1989: Kudin JI. A new way to size up a wound. American Journal of Nursing 1989: (2):206-7.
Lakovou, D. et al., "Integrated sensors for robotic laser welding," Proceedings of the Third International WLT-Conference on Lasres in Manufacturing, Jun. 2005, pp. 1-6.
Langemo et al., "Measuring Wound Length, Width, and Area: Which Technique?", Advances in Skin & Wound Care, Jan. 2008, pp. 42-45, vol. 21, No. I.
Langemo, DK et al "Comparison of 2 Wound Volume Measurement Methods" Advances in Skin & Wound Care Jul./Aug. 2001, vol. 14(4), 190-196.
Langemo, DK et al "Two-dimensional wound measurement: comparisan of 4 techniques" Advances in Wound Care Nov.-Dec. 1998, 11(7):337-43.
Laughton, C et al "A comparison of four methods of obtaining a negative impression of the foot" J Am Podiatr Med Assoc May 2002; 92 (5) :261-8.
Lee, et al, A Multi-stage Segmentation Method for Images of Skin Lesions; IEEE Conference Proceedings on Communication, Computers, and Signal Processing, ISBN 0-7803-2553-2, pp. 602-605, May 1995.
Levoy, et al. "The Digital Michelangelo Project: 3D Scanning of Large Statues," ACM, 2000.

(56) References Cited

OTHER PUBLICATIONS

Lewis 1997: Lewis P, McCann R, Hidalgo P, Gorman M. Use of store and forward technology for vascular nursing teleconsultation service. Journal of Vascular Nursing 1997. 15(4): 116-23. [A].

Lewies, JS, Achilefu S, Garbow JR, Laforest R, Welch MJ., Small animal imaging. current technology and perspectives for oncological imaging, Radiation Sciences, Washington University School of Medicine, Saint Louis, MO, USA, Eur J Cancer. Nov. 2002;38(16):2173-88.

Li, D. 2004, Database design and implementation for wound measurement system. Biophotonics, 2004: 42-43. [E].

Liu et al., "Wound measurement by curvature maps: a feasibility study," Physiol. Meas., 2006, pp. I 107-1123, vol. 27.

Lorimer, K "Continuity through best practice: design and implementation of a nurse-led community leg-ulcer service" Can J Nurs Res Jun. 2004, 36(2):105-12.

Lowery et al., "Technical Overview of a Web-based Telemedicine System for Wound Assessment," Advances in Skin & Wound Care, Jul./Aug. 2002, pp. 165-169, vol. 15, No. 4.

Lowson, S., "The safe practitioner: Getting the record straight: the need for accurate documentation," J Wound Care, Dec. 2004, vol. 13, No. 10, [retrieved on Dec. 17, 2004). Retrieved from the Internet: <URL: http://www.journalofwoundcare.com/nav?page=jowc.article&resource=I455125>, 2 pages.

Lucas, C., "Pressure ulcer surface area measurement using instant full-scale photography and transparency tracings," Advances in Skin & Wound Care, Jan./Feb. 2002, [retrieved on Jul. 28, 2006]. Retrieved from the Internet: < URL: http://www.findarticles.com/p/articles/mi _qa3977/is_200201 /ai_n904 . . . >, 7 pages.

Lunt, M.J., "Review of duplex and colour Doppler imaging of lower-limb arteries and veins," World Wide Wounds, 2000, [retrieved on Apr. 17, 2005]. Retrieved from the Internet: < URL: http://www.worldwidewounds.com/2000/sept/Michael-Lunt/Dopple . . . >, 6 pages.

Maglogiannis et al., "A system for the acquisition of reproducible digital skin lesions images," Technol and Health Care, 2003, pp. 425-441, vol. 11.

Malian et al., "MEDPHOS: A New Photogrammetric System for Medical Measurement," 2004, Commission V, WG V/3, 6 pages.

Mallat, S., et al. "Characterization of signals from multiscale edges", IEEE Trans Patt and Mech Int'l; 14:710-732; 1992.

Marchesini, R., et al. "In vivo Spectrophotometric Evaluation of Neoplastic and Non-Neoplastic Skin Pigmented Lesions. III. CCD Camera-Based Reflectance Imaging", Photochemistry and Photobiology, vol. 62, No. 1, pp. 151-154; 1995.

Marjanovic et al., "Measurement of the volume of a leg ulcer using a laser scanner," Physiol. Meas., 1998, pp. 535-543, vol. 19.

Mastronjcola et al., "Burn Depth Assessment Using a Tri-stimulus Colorimeter," Wounds—ISSN: !044-7946, Sep. 2005, pp. 255-258, vol. 17, No. 9.

McCardle, J., "Visitrak: wound measurement as an aid to making treatment decisions," The Diabetic Foot, Winter 2005, [retrieved onMar. 30, 2008). Retrieved from the Internet: < URL: http://findarticles.com/p/articles/mi_mOMDQ/is_4_8/ai_n16043804/print>, 4 pages.

Menzies, S., "The Morphologic Criteria of the Pseudopod in Surface Microscopy" Arch Dermatol, vol. 131, pp. 436-440, Apr. 1995.

Molnar et al., "Use of Standardized, Quantitative Digital Photography in a Multicenter Web-based Study," 2009, ePlasty, pp. 19-26, vol. 9.

Nachbar, et al., "The ABCD rule of dermatology", Journal of the American Academy of Dermatology, vol. 3, No. 4, pp. 551-559, Apr. 1994.

National Pressure Ulcer Advisory Panel, "FAQ: Photography for pressure ulcer documentation," 1 1P56, 4 pages.

National Pressure Ulcer Advisory Panel, Position Statement, 1998, [retrieved on Jan. 6, 2005]. Retrieved from the Internet: < URL: http://www.npuap.org/>, 2 pages (Pressure Ulcer Healing Chart attached, 2 pages).

Oduncu et al., "Analysis of Skin Wound Images Using Digital Color Image Processing: A Preliminary Communication," Lower Extremity Wounds, 2004, pp. 151-156, vol. 3, No. 3.

Pages, Jordi, et al., "Plane-to-plane positioning from image-based visual serving and structured light," Proceedings of 2004 IEEE/RSJ International Conference on Intelligent Robots and Systems, Sep. 28-Oct. 2, 2004, pp. 1004-1009.

Patete et al., "A non-invasive, three-dimensional, diagnostic laser imaging system for accurate wound analysis," Physiol. Meas., 1996, pp. 71-79, vol. 17.

Payne, C., "Cost benefit comparison of plaster casts and optical scans of the foot for the manufacture of foot orthoses," AJPM, 2007, pp. 29-31, vol. 41, No. 2.

Pehamberger, H., et al. "In vivo epiluminescence microscopy of pigmented skin lesions. I. Pattern analysis of pigmented skin lesions", Journal of American Academy of Dermatology, vol. 17, No. 4, pp. 571-583, Oct. 1987.

Plassman, et al. "Problems of Assessing Wound Size," Would healing Research Unit, University of Wales College of Medicine, Cardiff CF4 4XN, Wales, UK (1993) (Unpublished).

Plassmann et al., "MAVIS: a non-invasive instrument to measure area and vol. of wounds," Medical Engineering & Physics, 1998, pp. 332-338, vol. 20.

Plassmann, P., "Recording Wounds—Documenting Woundcare," Medical Computing Group, 1998, pp. 1-31.

Rogers et al., "Measuring Wounds: Which Stick to Use?", Podiatry Management, Aug. 2008, pp. 85-90.

Romanelli et al., "Technological Advances in Wound Bed Measurements," Wounds, 2002, pp. 58-66, vol. 14, No. 2, [retrieved on Apr. 8, 2005]. Retrieved from the Internet: < URL: http:/www.medscape.com/viewarticle/430900 _print>, 8 pages.

Russell, L., "The importance of wound documentation & classification," British J Nursing, 1999, pp. 1342-1354, vol. 8, No. 20.

Salcido, R., "The Future of Wound Measurement," Advances in Skin & Wound Care, Mar./Apr. 2003, pp. 54, 56, vol. 13, No. 2.

Salcido, R., "Pressure Ulcers and Wound Care," Physical Medicine and Rehabilitation, eMedicine, 2006, [retrieved on]. Retrieved from the Internet: < URL: http://www.emedicine.com/pmr/topic 179.htm>, 25 pages.

Salmhofer, et al., "Wound teleconsultation in patients with chronic leg ulcers," 2005.

Sani-Kick et al., "Recording and Transmission of Digital Wound Images with the Help of a Mobile Device," 2002, 2 pages.

Santamaria et al., "The effectiveness of digital imaging and remote expert wound consultation on healing rates in chronic lower leg ulcers in the Kimberley region of Western Australia," Primary Intention, May 2004, pp. 62-70, vol. 12, No. 2.

Schindelwof, et al. "Comparison of classification rates for conventional and dermatoscopic images of malignant and benign melanocytic lesions using computerized colour image analysis", Eur J Dermatol, vol. 3, No. 4, pp. 299-303, May 1993.

Schindewolf, T., et al. "Classification of Melanocytic Lesions with Color and Texture Analysis Using Digital Image Processing", The International Academy of Cytology, Analytical and Quantitative Cytology and Histology, vol. 15, No. 1, pp. 1-11, Feb. 1993.

Schindewolf, T., et al. "Evaluation of different image acquisition techniques for a computer vision system in the diagnosis of malignant melanoma", Journal of the American Academy of Dermatology, vol. 31, No. 1, pp. 33-41, Jul. 1994.

Schultz et al., "Wound bed preparation: a systematic approach to wound management," Wound Repair and Regeneration, Mar./Apr. 2003, p. SI-S28, vol. 11, No. 2, Supplement.

Shaw et al., "An Evaluation of Three Wound Measurement Techniques in Diabetic Foot Wounds," Diabetes Care, 2007, [retrieved on Mar. 30, 2008]. Retrieved from the Internet: < URL: http://care.diabetesjournals.org/cgi/content/full/30/1 0/2641?ck=nck>, 5 pages.

Sheehan et al., "Percent Change in Wound Area of Diabetic Foot Ulcers Over a 4-Week Period Is a Robust Predictor of Complete Healing in a 12-Week Prospective Trial," Diabetes Care, Jun. 2003, pp. 1879-1882, vol. 26, No. 6.

Sheng, Chao, Brian W. Pogue, Hamid Dehghani, Julia A. O'Hara, P. J. Hoopes, Numerical light dosimetry in murine tissue: analysis of tumor curvature and angle of incidence effects upon fluence in the

(56) References Cited

OTHER PUBLICATIONS tissue, Proc. SPIE, vol. 4952, 39 (2003), DOI:10.1117/12.474081, Online Publication Date: Jul. 28, 2003.

Smith & Nephew, "Leg ulcer guidelines: a pocket guide for practice," National Guideline Clearinghouse, U.S. Dept of Health & Human Services, 2002, [retrieved on Jan. 10, 2012]. Retrieved from the Internet: < URL: http://guidelines.gov/content.aspx?id=9830 &search=Pressure+Ulcer>, 17 pages.

Smith & Nephew, "Visitrak Wound Measurement Device," Wound Management, [retrieved on Apr. 7, 2005]. Retrieved from the Internet: < URL: http://wound.smith-nephew.com/us/node.asp? NodeId=3 I 20>, 7 pages.

Smith & Nephew, "Guidelines for the Management of Leg Ulcers in Ireland" www.smith-nephew.com.

Smith et al., "Three-Dimensional Laser Imaging System for Measuring Wound Geometry," Lasers in Surgery and Medicine, 1998, pp. 87-93, vol. 23.

Sober, et al., "Computerized Digital Image Analysis: An Aid for Melanoma Diagnosis", The Journal of Dermatology, vol. 21, pp. 885-890, 1994.

Solomon et al., "The use of video image analysis for the measurement of venous ulcers," British J Dermatology, 1995, pp. 565-570, vol. I 33.

Steiner, A., "In vivo epiluminescence microscopy of pigmented skin lesions. II. Diagnosis of small pigmented skin lesions and early detection of malignant melanoma", Journal of the American Academy of Dermatology, vol. 17, No. 4, pp. 584-591; Oct. 1987.

Stoecker, et al. "Automatic Detection of Asymmetry in Skin Tumors" Computerized Medical Imaging and Graphics, vol. 16, No. 3, pp. 191-197, 1992.

Takiwaki, et al., "A rudimentary system for automatic discrimination among basic skin lesions on the basis of color analysis of video images", Journal of the American Academy of Dermatology, vol. 32, No. 4, pp. 600-604, Apr. 1995.

Tellez, R., "Managed Care Making Photo Documentation a Wound Care Standard," Wound Care, 1997, [retrieved on Aug. 29, 2005]. Retrieved from the Internet: <URL: http://woundcare.org/newsvol2n4/arl.htm>, 2 pages.

Thali, M.J., et al. "Optical 3D surface digitizing in forensic medicine: 3D documentation of skin and bone injuries." Forensic Science International, 2003.

Thawer et al., "A Comparison of Computer-Assisted and Manual Wound Size Measurement, " Ostomy Wound Management, Oct. 2002, pp. 46-53, vol. 48, No. IO.

Treuillet et al., "Three-Dimensional Assessment of Skin Wounds Using a Standard Digital Camera," IEEE Transactions on Medical Imaging, May 2009, pp. 752-762, vol. 28, No. 5.

Umbaugh et al., "Automatic Color Segmentation Algorithms with Application to Skin Tumor Feature Identification", IEEE Engineering in Medicine and Biology, pp. 75-82, Sep. 1993.

Umbaugh, et al., "An Automatic Color Segmentation Algorithm with Application to Identification of Skin Tumor Borders", Computerized Medical Imaging and Graphics, vol. 16, No. 3, pp. 227-235, May-Jun. 1992.

Umbaugh, et al., "Automatic Color Segmentation of Images with Application to Detection of Variegated Coloring in Skin Tumors", IEEE Engineering in Medicine and Biology Magazine, Dec. 1989, pp. 43-52.

Van Zuijlen et al., "Reliability and Accuracy of Practical Techniques for Surface Area Measurements of Wounds and Scars," Lower Extremity Wounds, 2004, pp. 7-11, vol. 3, No. I.

Vermolen et al., "A simplified model for growth factor induced healing of circular wounds," 2005, pp. 1-15.

Voigt, H., et al. "Topodermatographic Image Analysis for Melanoma Screening and the Quantitative Assessment of Tumor Dimension Parameters of the Skin", Cancer, vol. 75, No. 4, Feb. 15, 1995.

Walker, N, Rogers A, Birchall N, Norton R, MacMahon S, Leg ulcers in New Zealand: age at onset, recurrence and provision of care in an urban population. NZ Med J; 2002; 115(1156):286-9.

Walker, N, Vandal A, Holden K, Rogers A, Birchall N, Norton R, Triggs C, MacMahon S. Does capture-recapture analysis provide more reliable estimates of the incidence and prevalence of leg ulcers in the community? Aust NZJ Public Health 2002; 26(5):451-5.

Walker, N., Rodgers A, Birchall N, Norton R, MacMahon S. The occurrence of leg ulcers in Auckland: results of a population-based study. NZ Med J; 2002: 115(1151): 159-162.

Wallenstein et al., "Statistical analysis of wound-healing rates for pressure ulcers," Amer J Surgery, Jul. 2004 (Supplement), pp. 73S-78S, vol. 188.

Wang et al., "A comparison of digital planimetry and transparency tracing based methods for measuring diabetic cutaneous ulcer surface area," Zhongguo Xiu Fu Chong Jian Wal Ke Za Zhi, May 2008, pp. 563-566, vol. 22, No. 5, [retrieved on Sep. 15, 2009]. Retrieved from the Internet: <URL: http://www.ncbi.nlm.nih.gov/pubmed/ 1 8630436?ordinalpos= I &itool=E . . . >, I page.

Wendelken et al., "Key Insights on Mapping Wounds With Ultrasound," Podiatry Today, Jul. 2008, [retrieved on Jul. 14, 2008]. Retrieved from the Internet: <URL: http://www.podiatrytoday.com/article/5831>, 5 pages.

Wilbright, W.A., The Use of Telemedicine in the Management of Diabetes-Related Foot Ulceration: A Pilot Study, Advances in Skin & Wound Care, Jun. 2004, [retrieved on Jul. 28, 2006]. Retrieved from the Internet: <URL: http://www.findarticles.com/p/articles/mi_qa3977/is_200406/ai_n942 . . . >, 6 pages.

Wild et al., "Wound healing analysis and measurement by means of colour segmentation," ETRS Poster Presentation V28, Sep. 15, 2005, V28-I 7, 1 page.

Williams, C., "The Verge Videometer wound measurement package," British J Nursing, Feb./Mar. 2000, pp. 237-239, vol. 9, No. 4.

Woodbury et al., Pressure ulcer assessment instruments: a critical appraisal, Ostomy Wound Management, May 1999, pp. 48-50, 53-55, vol. 45, No. 5, [retrieved on Dec. 8, 2005]. Retrieved from the Internet: <URL: http://gateway.ut.ovid.com.ezproxy.otago.ac.nzigw2/ovidweb.cgi>, 2 pages.

Woodbury, M.G., "Development, Validity, Reliability, and Responsiveness of a New Leg Ulcer Measurement Tool," Advances in Skin & Wound Care, May 2004, [retrieved on Jul. 28, 2006]. Retrieved from the Internet.

Zhao, et al, The Classification of the Depth of Burn Injury Using Hybrid Neural Network; IEEE Conference on Engineering in Medicine and Biology Society, ISBN 0-7803-2475-7; vol. 1, pp. 815-816, Sep. 1995.

Zimmet, "Venous Leg Ulcers: Evaluation and Management," American College of Phlebology. 1998.

Notice of Allowance dated Feb. 24, 2021, U.S. Appl. No. 15/816,862, 18 pages.

Extended European Search Report for European Application No. EP22204772.2 filed Apr. 3, 2018, dated Apr. 13, 2023, 6 pages.

Final Office Action dated Jul. 13, 2023, U.S. Appl. No. 17/398,883, 22 pages.

* cited by examiner

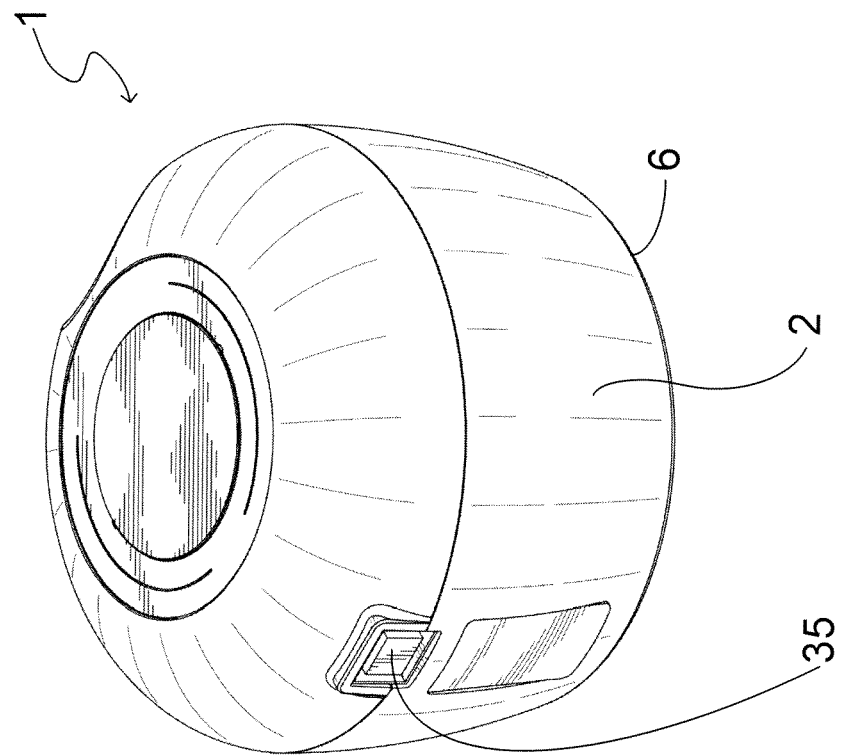
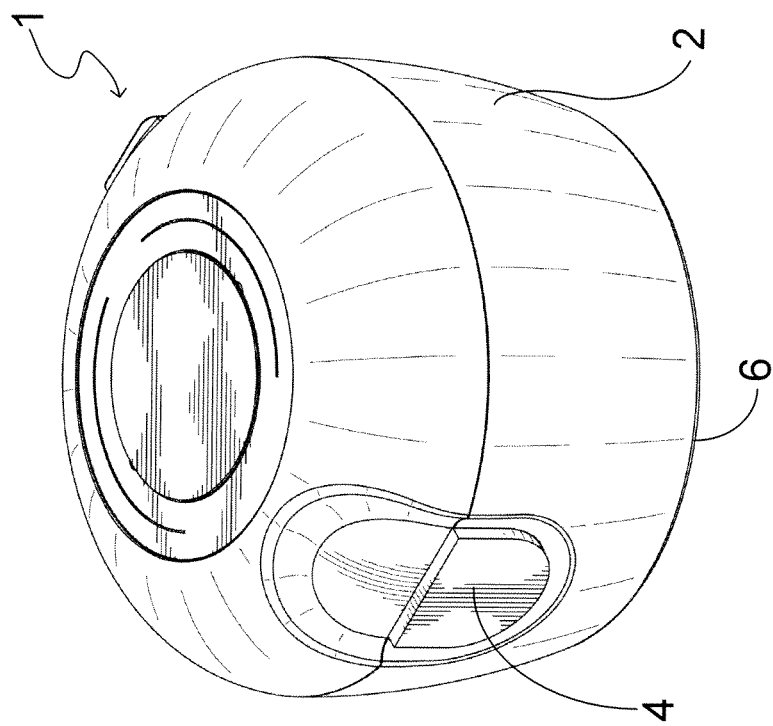

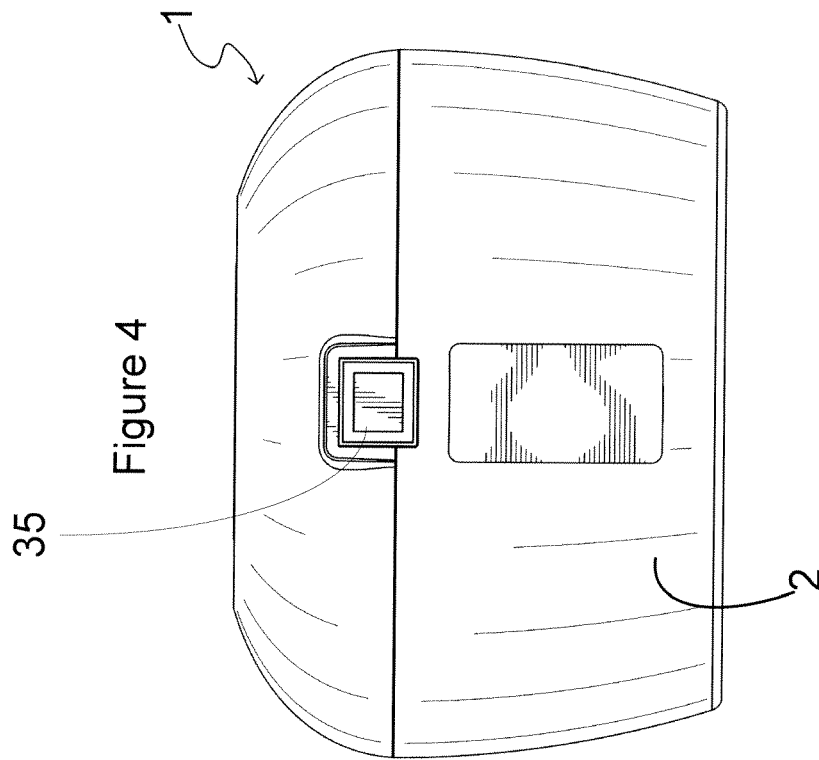
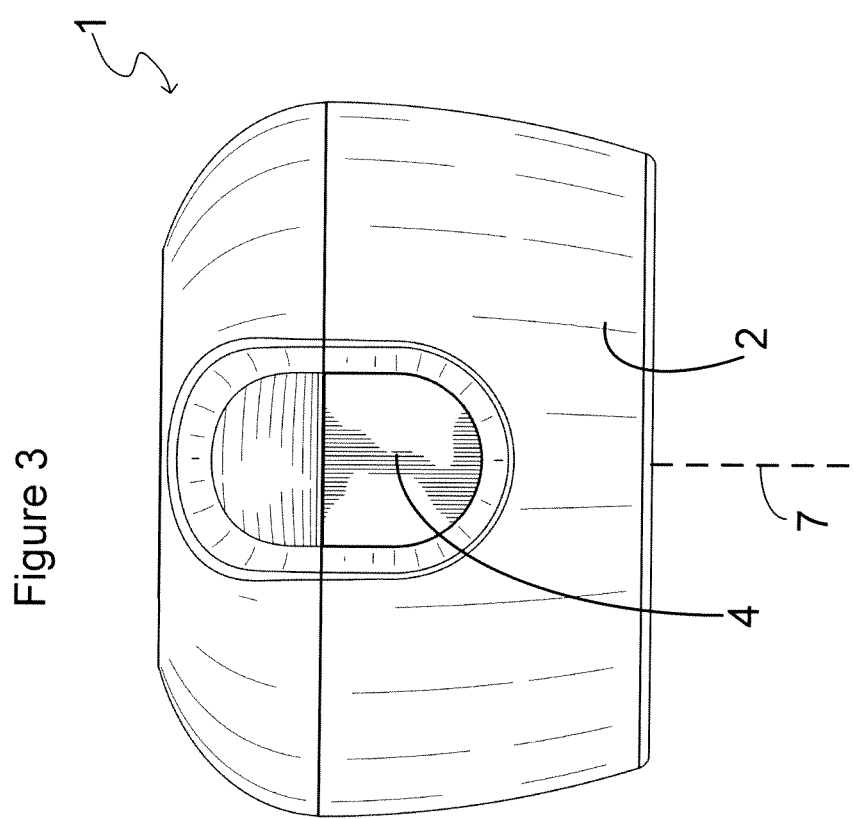

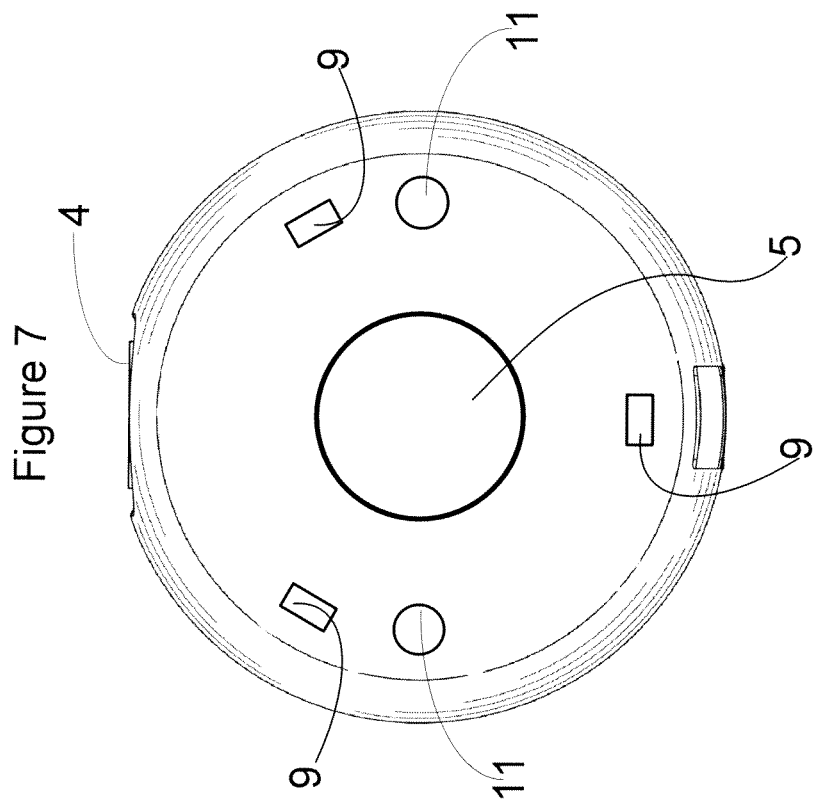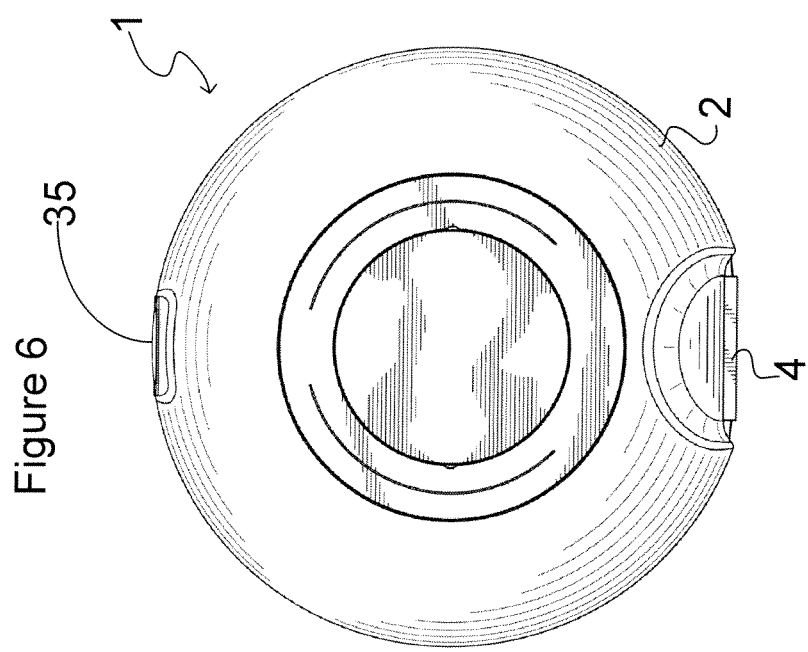

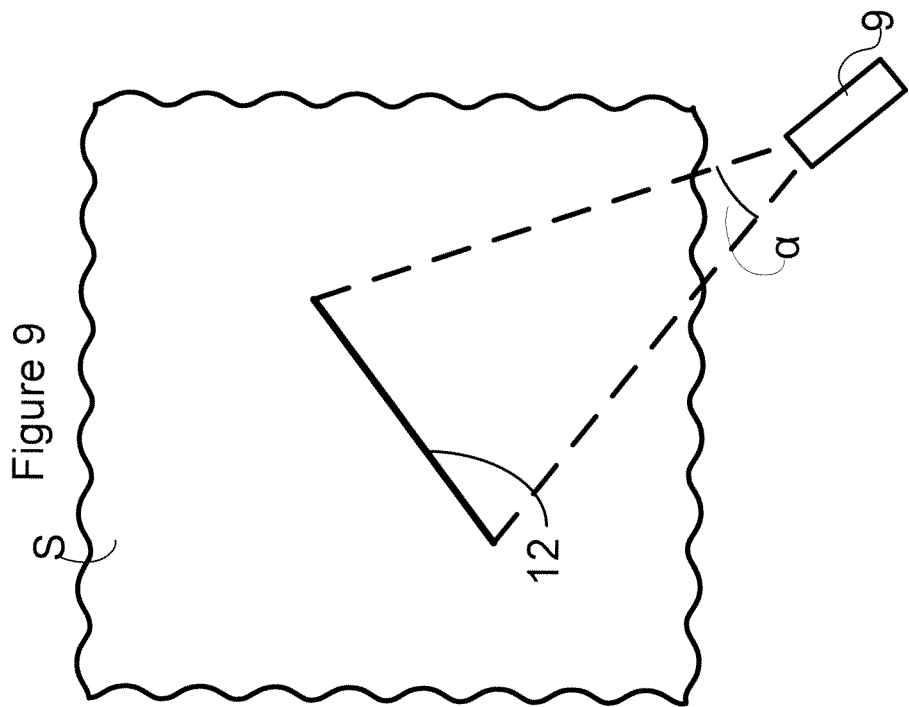
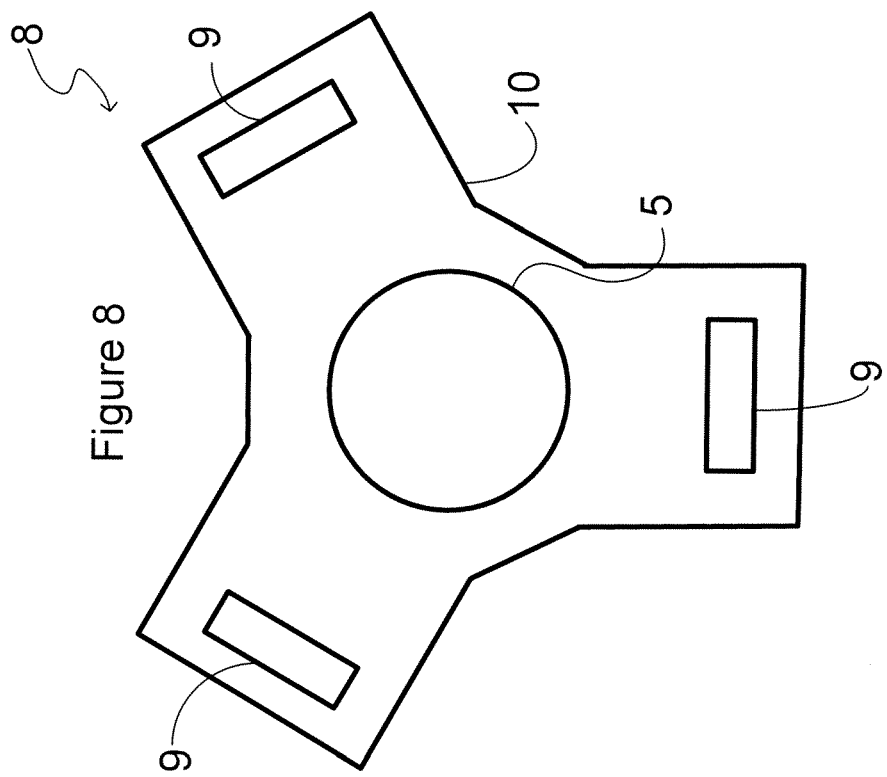

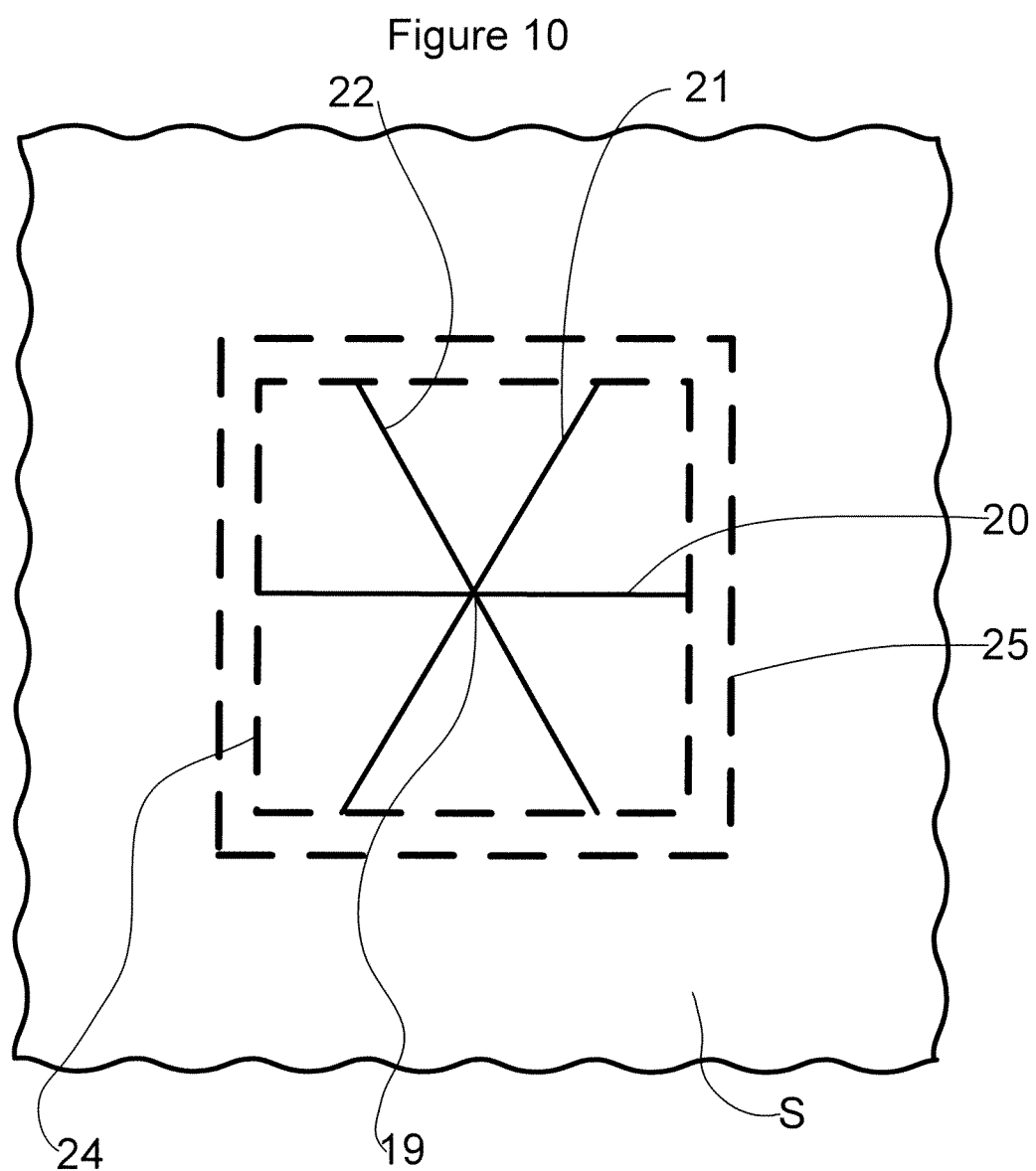

HANDHELD SKIN MEASURING OR MONITORING DEVICE

CROSS-REFERENCE TO RELATED APPLICATIONS

This application is a continuation of U.S. patent application Ser. No. 15/851,580, filed Dec. 21, 2017, which is a continuation of U.S. patent application Ser. No. 14/931,465, filed Nov. 3, 2015, now U.S. Pat. No. 9,861,285, which is a continuation of U.S. patent application Ser. No. 13/686,738, filed Nov. 27, 2012, now U.S. Pat. No. 9,179,844, which claims the benefit of U.S. Provisional Patent Application No. 61/564,089, filed Nov. 28, 2011. Each of these applications is incorporated herein by reference in its entirety.

FIELD OF THE INVENTION

The invention relates to devices and methods for monitoring or measuring skin features, such as wounds, ulcers, sores, lesions, tumors, bruises, burns, psoriasis, keloids, skin cancers, erythema, cellulitis or the like.

BACKGROUND TO THE INVENTION

Reference to any prior art in this specification does not constitute an admission that such prior art forms part of the common general knowledge.

Various techniques have been used to monitor wounds, ulcers, sores, lesions, tumors etc. (herein referred to collectively as "wounds") both within hospitals and outside hospitals (e.g. in domiciliary based care, primary care facilities etc.). Manual techniques are typically labor-intensive and require examination and contact by skilled personnel. Such measurements may be inaccurate and there may be significant variation between measurements made by different personnel. Further, traditional approaches may not preserve any visual record for review by an expert or for subsequent comparison.

A number of techniques for the automated monitoring of wounds have been proposed; see for example U.S. Pat. Nos. 6,101,408, 6,873,340, 4,535,782 and 5,967,979. A common approach is to place a reference object next to the wound and determine the size of the wound utilizing the scale of the reference object. It is often undesirable to place a reference object near to a wound and this requires an additional cumbersome step for a user and risks contamination of the wound. Further, when the target is not in the plane of the wound, or if the wound is not planar, there will be errors in any area calculation.

Other systems, such as that described in US2004/0136579, require the camera always to be positioned with a guide against the patient's skin. While this consistently positions the camera a desired distance from the surface to be photographed and therefore sets the scale of the image, it is unwieldy and requires undesirable contact with the skin, risking contamination of the wound.

Many prior systems also suffer from high cost, which limits uptake of the systems.

The Applicant's prior specification published as US2009/213213 proposed a handheld surface measuring device based on a structured light device. (The contents of that specification are hereby incorporated by reference herein.) A laser fan-beam was projected at a known angle to a camera optical axis and the resulting image data could be used to measure wound properties such as area or depth. However, the Applicant has recognized that further improvements in wound measurement are possible.

It is an object of the invention to provide an improved device for monitoring or measuring skin features, or to at least provide the public with a useful choice.

SUMMARY OF THE INVENTION

The invention provides a handheld skin monitoring or measuring device, method and system. The invention relies on structured light techniques and in some embodiments uses a structured light arrangement configured to project three or more laser fan beams such that the laser fan beams cross at a crossing point in front of the camera.

In a first aspect the invention provides a handheld skin monitoring or measuring device, including: a camera having a camera optical axis; and a structured light arrangement configured to project three or more laser fan beams such that the laser fan beams cross at a crossing point in front of the camera.

Preferably the structured light arrangement is configured to project the laser fan-beams such that a pattern formed by the laser fan-beams on a skin surface varies with a distance between the device and the skin surface, and wherein the pattern is a predetermined pattern when the device is at a distance from the skin surface within an optimum range, such that a user is enabled to position the handheld skin monitoring or measuring device at a distance from the skin surface within the optimum range by adjusting the distance such that the predetermined laser pattern is formed on the surface.

Preferably the predetermined pattern includes the laser fan-beams crossing at the crossing point, and a user is enabled to position the handheld skin monitoring or measuring device at a distance from a skin surface within an optimum range by aligning the crossing point with the skin surface.

Preferably the camera has a camera field of view and the three or more laser fan beams subtend fan beam angles corresponding to the camera field of view, such that the ends of the laser beams projected onto a skin surface define a region that substantially corresponds to an image frame of the camera.

Preferably the region occupies between 80% and 120% of the area of the image frame.

Preferably the device has no display.

Preferably the device further includes a capture switch, the device being arranged to capture data on actuation of the capture switch.

Preferably the device further includes a communications port, the device being configured to transmit data captured by the camera from the communications port.

Preferably the device further includes memory configured to store data captured by the camera.

Preferably the device further includes one or more light sources configured to illuminate the skin surface.

Preferably the device is configured to capture at least the following data in response to a single user capture instruction: an image with the laser fan beams switched off; and at least three images each including one or more laser fan beams, such that each laser fan beam is unambiguously identifiable.

Preferably the device further includes a substantially spherical housing dimensioned to fit a user's cupped hand, the camera and structured light arrangement being mounted in the housing.

Preferably the structured light arrangement is configured to project three laser fan beams from sources distributed evenly around the camera optical axis such that the three laser fan beams form an equilateral triangle in any plane that is perpendicular to the camera optical axis and does not include the crossing point.

Preferably the structured light arrangement is configured to project three laser fan beams.

In a second aspect the invention provides a handheld skin monitoring or measuring device, including: a camera having a camera optical axis and a camera field of view; and a structured light arrangement configured to project three or more laser fan beams such that the laser fan beams cross at a crossing point in front of the camera, the laser fan beams subtending fan beam angles corresponding to the camera field of view, such that the ends of the laser beams projected onto a skin surface define a region that substantially corresponds to an image frame of the camera.

Preferably a user can position the handheld skin monitoring or measuring device at a distance from a skin surface within an optimum range by adjusting the distance such that a predetermined laser pattern is projected onto the surface.

Preferably a user can position the handheld skin monitoring or measuring device at a distance from a skin surface within an optimum range by aligning the crossing point with the skin surface.

Preferably the region occupies between 80% and 120% of the area of the image frame.

Preferably the device has no display.

Preferably the device further includes a capture switch, the device being arranged to capture data on actuation of the capture switch.

Preferably the device further includes a communications port, the device being configured to transmit data captured by the camera from the communications port.

Preferably the device further includes memory configured to store data captured by the camera.

Preferably the device further includes one or more light sources configured to illuminate the skin surface.

Preferably the device is configured to capture at least the following data in response to a single user capture instruction: an image with the laser fan beams switched off; and at least three images each including one or more laser fan beams, such that each laser fan beam can be unambiguously identified.

Preferably the device further includes a substantially spherical housing dimensioned to fit a user's cupped hand, the camera and structured light arrangement being mounted in the housing.

Preferably the structured light arrangement is configured to project three laser fan beams from sources distributed evenly around the camera optical axis such that the three laser fan beams form an equilateral triangle in any plane that is perpendicular to the camera optical axis and does not include the crossing point.

Preferably the structured light arrangement is configured to project three laser fan beams.

In a further aspect the invention provide a method of capturing data concerning a skin feature using a handheld skin monitoring or measuring device, including: a camera having a camera optical axis and a camera field of view; a structured light arrangement configured to project three or more laser fan beams such that the laser fan beams cross at a crossing point in front of the camera; the laser fan beams subtending fan beam angles corresponding to the camera field of view, such that the laser beams projected onto a skin surface define a region that substantially corresponds to an image frame of the camera; the method including: directing the handheld skin monitoring or measuring device towards a skin surface; projecting at least some of the laser fan beams using the structured light arrangement; and adjusting a position of the handheld skin monitoring or measuring device such that laser fan beams define a desired image region on the skin surface; and capturing data using the camera.

In a further aspect the invention provides a display-less handheld skin monitoring or measuring device including: a substantially spherical housing dimensioned to fit the cupped hand of a user; a camera mounted in the housing; a structured light arrangement mounted in the housing and configured to project three or more laser fan beams such that the laser fan beams cross at a crossing point in front of the camera; and a communications link configured to transmit image data captured by the camera.

BRIEF DESCRIPTION OF THE DRAWINGS

The invention will now be described by way of example only, with reference to the accompanying drawings, in which:

FIG. 1 is a perspective view of a handheld skin measuring or monitoring device according to one embodiment;

FIG. 2 is a second perspective view of the device of FIG. 1;

FIG. 3 is a first side view of the device of FIG. 1;

FIG. 4 is a second side view of the device of FIG. 1;

FIG. 6 is a top view of the device of FIG. 1;

FIG. 7 is a cut-away top view of the device of FIG. 1;

FIG. 8 shows the mounting of the camera and structured light according to one embodiment;

FIG. 9 shows a laser fan-beam projector projecting a laser fan-beam onto a surface;

FIG. 10 shows a laser pattern projected onto a surface by the device of FIG. 1;

DETAILED DESCRIPTION OF PREFERRED EMBODIMENTS

Figure 1A:
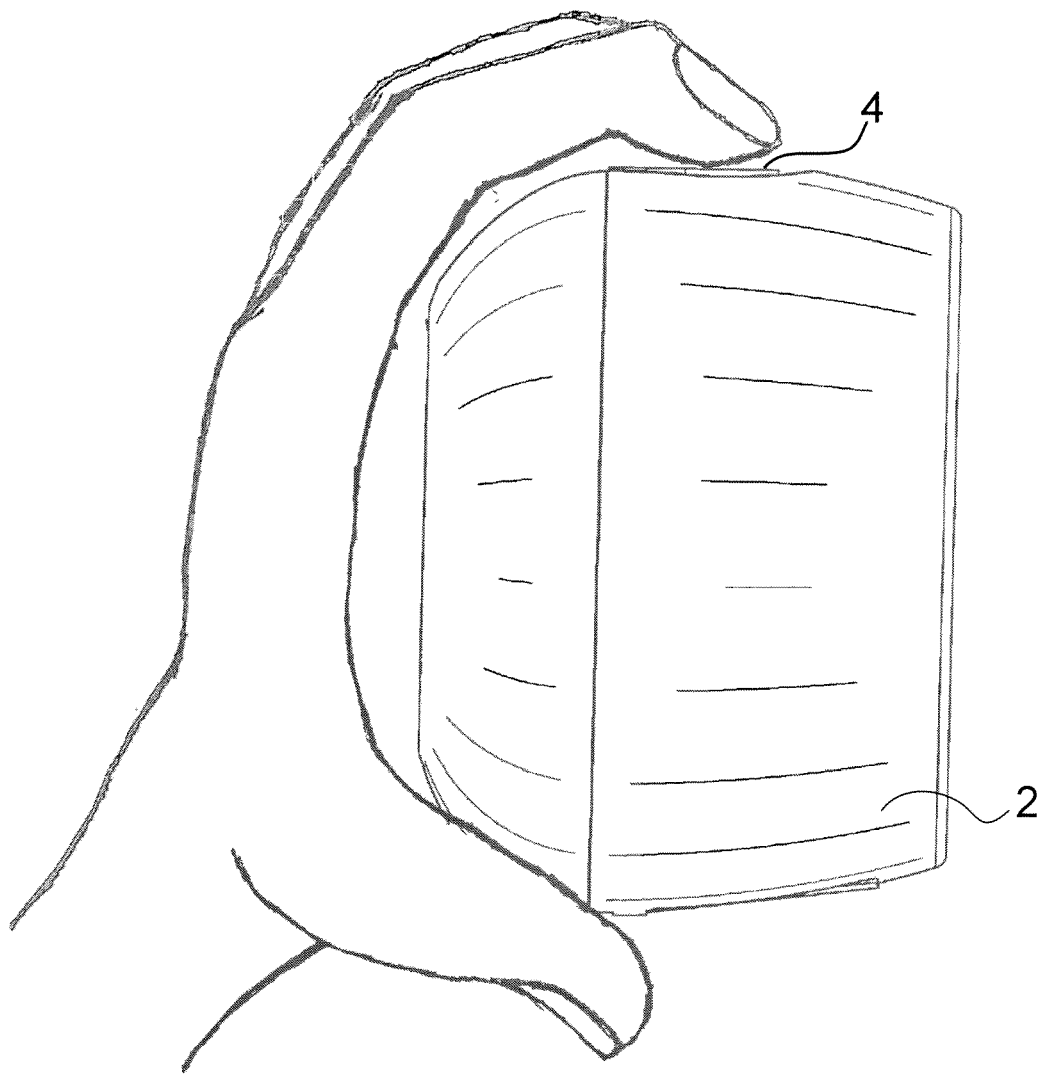
FIG. 1*a* shows the device of FIG. 1 in the cupped hand of a user.
Figure 5:
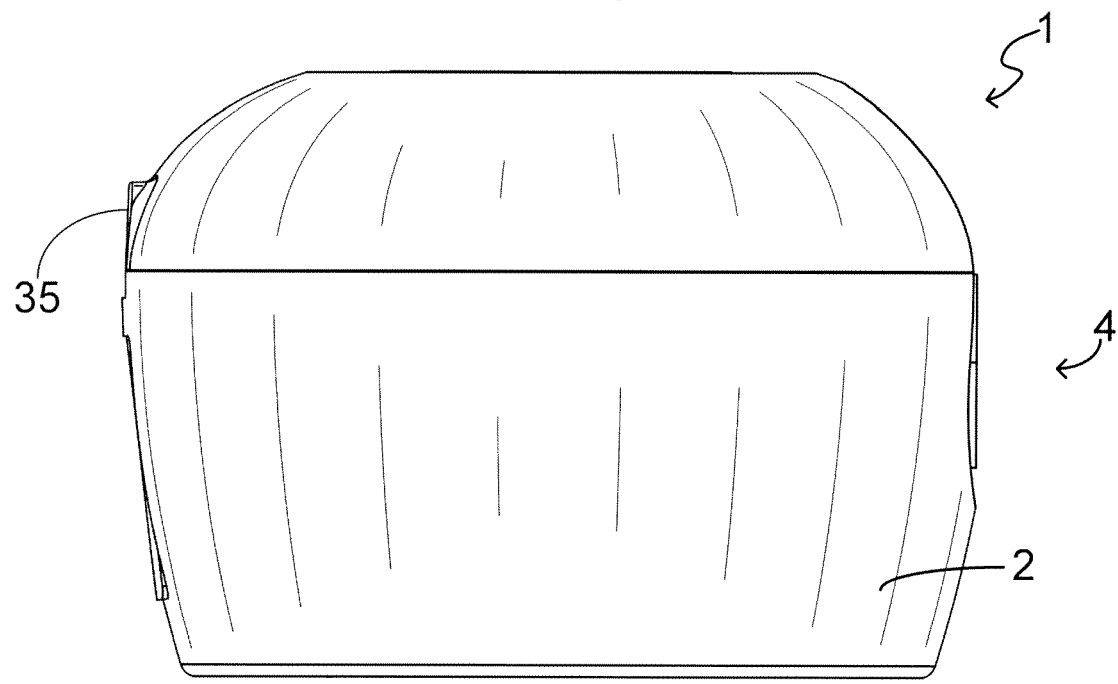
FIG. 5 is a third side view of the device of FIG. 1.

The invention relates to devices for monitoring or measuring skin features, such as wounds, ulcers, sores, lesions, tumors, bruises, burns, psoriasis, keloids, skin cancers, erythema, cellulitis or the like.

FIGS. 1 to 7 show a skin measuring or monitoring device 1 according to one embodiment. The device includes a housing 2 that has a generally circular or elliptical cross-section, as shown in FIG. 6, and a substantially spherical shape, as shown in e.g. FIGS. 1 and 2. In this specification "substantially spherical shape" does not exclude the possibility of flat areas, such as the front face 6 of the device shown in the drawings, recessed areas around the camera lens etc. In the embodiment shown the substantially spherical housing 2 has a generally curved rear surface to fit a user's hand, while the front face 6 of the device is flat.

The housing 2 is made to be held in the cupped hand of a user, such that the user's fingers extend around the sides of the housing 2 and a user's finger or thumb (preferably the index or middle finger) can be positioned on capture button 4, as shown in FIG. 1a. This shape allows the device 1 to be positioned with a significant degree of flexibility. This is important because the device may be used to capture images for skin features in difficult to access areas, such as the underside of an immobile patient's leg. This is also useful where there is limited space available to access the skin feature. This shape also allows convenient one-handed operation, which in turn allows the user's other hand to be used to aid positioning of an immobile patient or for any other necessary purpose.

In one embodiment the housing 2 may have a diameter in the range around 85 to 115 mm (around 3.3 to 4.5 inches), preferably around 100 mm (around 3.9 inches). In the embodiment shown this diameter is measured transverse to the optical axis 7 (FIG. 3). This measurement provides a comfortable fit for most hand sizes. Parallel to the optical axis the housing 2 may measure around 70 mm (around 2.7 inches), this measurement being less than the diameter due to the flattened front face 6 of the device 1. The measurements of the housing are preferably sufficiently small to be comfortably held and sufficiently large that the average user's fingers and thumbs will not contact the optical apertures on the front surface, in the normal holding position shown in FIG. 1A.

The device 1 includes a camera 5 (FIG. 7) that may be mounted in the housing 2. The camera optical axis 7 extends forwards of the housing 2, as shown in FIG. 3.

The camera 5 may be mounted in fixed relation to a structured light arrangement 8, as shown in FIG. 8. The structured light arrangement 8 is configured to project three laser fan beams or stripes. The structured light arrangement 8 may include three laser fan-beam projectors 9 evenly distributed around the camera optical axis 7. In FIG. 8, the camera 5 and structured light arrangement 8 are mounted in a rigid framework 10. The laser fan-beam projectors 9 are preferably adjustably mounted to allow factory calibration of the structured light arrangement. For example, the laser fan-beam projectors 9 may be mounted using set-screws allowing small adjustments in the laser fan-beams.

FIG. 7 is a front view of the device 1 with the framework 10 omitted. The device may also include a transparent window, such that the camera and/or structured light arrangement is positioned behind the window. This figure shows the structured light projectors 9 and camera 5. In addition this figure shows a number of light sources 11. These light sources 11 may be used to illuminate the skin surface during some image capture steps, as will be described further below. These may be any suitable diffuse light sources for illumination of a skin surface. In one embodiment white light emitting diodes (LEDs) may be used.

A laser fan-beam emitted by a single laser fan-beam projector 9 is shown in FIG. 9. The laser fan-beam projector 9 is directed towards a surface S. The projected laser beam has a fan-beam angle $\propto$ and is relatively thin, such that a laser line 12 is projected onto a flat surface S. The shape of the fan-beam on a non-flat surface will be more complex, as will be discussed further below. The length of the laser fan-beam line 12 will depend on the fan-beam angle $\propto$, the distance between the laser fan-beam projector 9 and the surface S, and the relative angle between the laser fan-beam projector 9 and the surface S.

The laser fan-beam angle $\propto$ may be adjusted using an adjustable mask. For example, a small set screw may be positioned at each side of the projector 9. Adjustment of the two set-screws allows the fan-beam angle to be narrowed or broadened in the factory at the time of manufacturing or assembly.

The three laser fan-beams are arranged at an angle towards the optical axis. As shown in FIGS. 7 and 8 the laser fan-beam projectors 9 are mounted at a distance from the optical axis. This means that the three fan-beams will cross at a crossing point in front of the camera. This point may be on the optical axis. However, this will depend on the alignment of the camera and laser fan-beam projectors.

Figure 11:
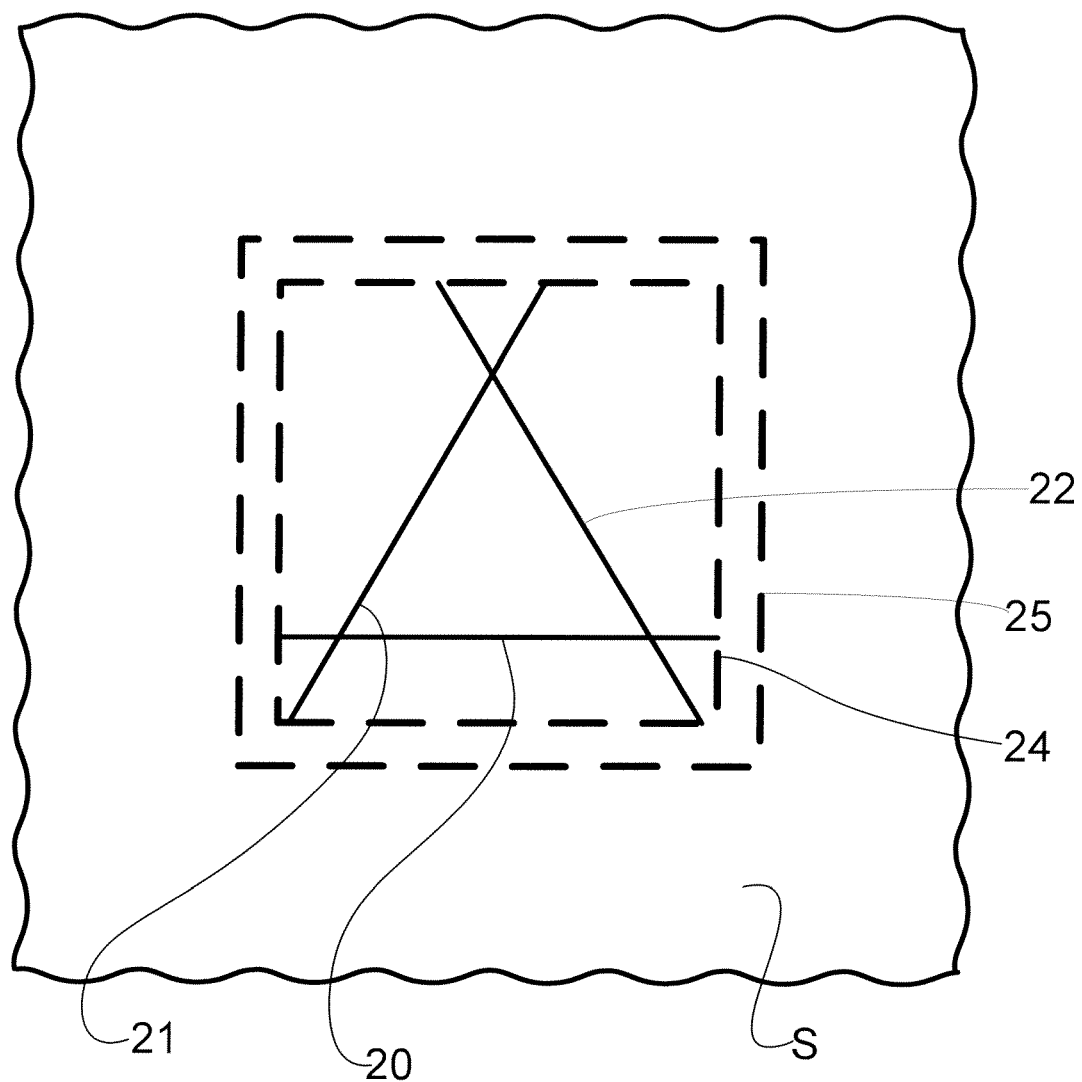
FIG. 11 shows a further laser pattern projected onto a surface by the device of FIG. 1.
Figure 12:
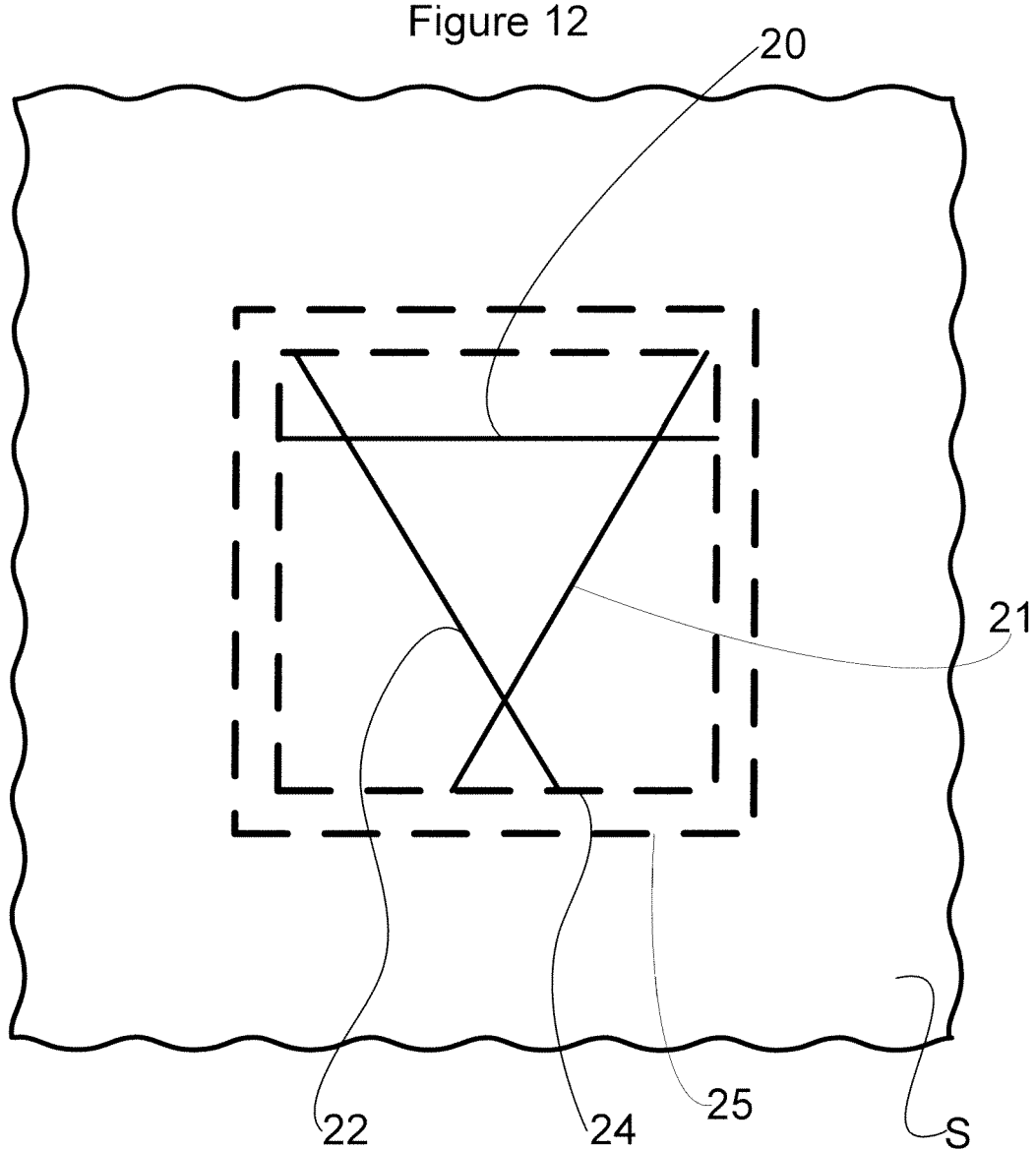
FIG. 12 shows a further laser pattern projected onto a surface by the device of FIG. 1.

FIG. 10 shows a laser pattern projected by the structured light arrangement onto a flat surface S. This pattern, and the patterns of FIGS. 11 and 12, are ideal patterns that are projected with the device perfectly perpendicular to the flat surface S. These patterns are included in order to illustrate the working of the device. In practical situations, making measurements on the skin surface, more complicated patterns will result.

Returning to FIG. 10, the flat surface S is arranged perpendicular to the camera optical axis and at the crossing point 19 of the three laser fan-beams 20, 21, 22. The crossing point may be at a distance in front of the device that corresponds to the mid-point of an optimum measurement range. The optimum measurement range may lie between optimum measurement limits, with the crossing point 19 at or near to the mid-point of those limits. The optimum measurement range may be a range in which acceptable focus and/or exposure are expected to be obtained. This will depend on the camera used.

This relationship between the crossing point 19 and the optimum measurement range provides convenient and intuitive user-positioning of the device 1. A user may simply position the device such that the crossing point 19 falls on the skin surface. In this embodiment the user is enabled, or guided, to align the device such that a predetermined pattern in the form of three stripes crossing at a point is seen on the skin. The user then knows that the device is at or near an optimum measurement distance, or within an optimum measurement range. There is no need for the user to look at some other alignment device such as a display screen on an attached computer. Alignment is possible using the light pattern itself.

In one embodiment the laser fan-beams are also arranged to mark out an image capture region. In FIG. 10 the laser fan-beams 20, 21, 22 have lengths such that their end points mark out a region indicated by dashed rectangle 24. Dashed rectangle 25 corresponds to the camera field of view. Dashed rectangles 24, 25 are not projected onto the surface, but are shown in the drawings to illustrate the working of the invention.

The position of the ends of the laser lines on the surface is governed by the laser fan-beam angles subtended by the lines and the distance between the device and the surface.

The laser line position also depends on the angle of the fan-beam with respect to the optical axis.

This feature provides convenient and intuitive framing. A user can align the device such that the laser fan-beams 20, 21, 22 define a region 24 that includes a skin feature. Desirably the region will include some healthy skin around the skin feature. As this region 24 corresponds to the camera field of view 25, the images captured by the camera will be appropriately framed. Note that no viewfinder or display is required, and indeed in preferred embodiments the device is display-less. This has a number of advantages. A display-less device has a lower cost and lower power consumption than a device with a display.

Further, when measuring skin features in awkward places (e.g. on the underside of a leg that is being held up by the patient or an assistant) a display on the device is not always visible. However, the skin feature itself is usually visible. In some embodiments a remote display, connected by a wired or wireless connection, may be used. However, in preferred embodiments the device does not include a display, but uses the structured light elements themselves to assist in framing, for example as described above.

Preferably the region 24 is defined by the ends of the laser fan-beams, which span the region 24, passing through the inner part of region 24. This provides framing as discussed above, but also provides good sampling of structured light data from a central part of the image frame.

The region 24 preferably defines an area that corresponds to the camera frame area plus or minus 20%, more preferably plus or minus 15%. As the fan-beam is projected with a fan-beam angle ∝ (FIG. 9), this framing can be used over various ranges from the device to the skin surface. The correspondence of the region 24 to the frame 25 may vary with range while remaining within the above limits.

While the device may be positioned with the crossing point at the skin surface, as shown in FIG. 10, the device may also be used at other ranges. FIG. 11 shows the laser pattern on a flat surface S when the device is positioned closer to the surface S than in the position of FIG. 10. Here the three laser fan-beams 20, 21, 22 form an equilateral triangle and may extend beyond the triangle to define the region 24.

FIG. 12 shows the laser pattern on a flat surface S when the device is positioned further away from the surface S than in the position of FIG. 10. Here the three laser fan-beams 20, 21, 22 also form an equilateral triangle and may extend beyond the triangle to define the region 24. The triangle of FIG. 12 is inverted when compared to the triangle of FIG. 11.

Figure 13:
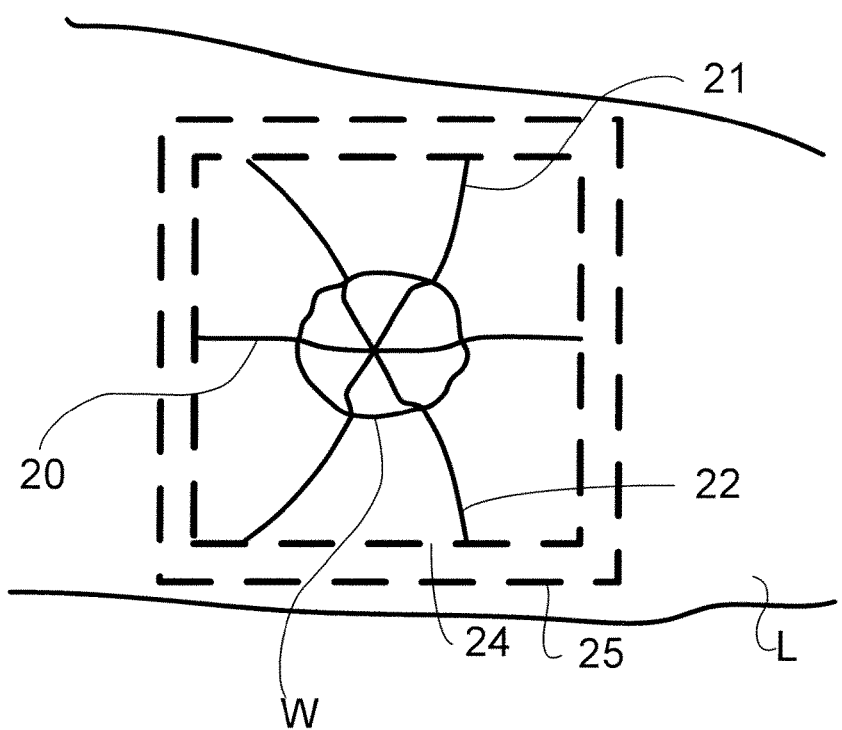
FIG. 13 shows a laser pattern projected onto a skin surface and skin feature by the device of FIG. 1.

FIG. 13 shows the laser pattern that may be projected onto a skin surface. In this example a patient has an ulcer or other wound W on his or her leg L. The leg L has a natural curvature from a high point along the centre and falling away towards the top and bottom of the image frame 25.

In addition, in this example the wound W is recessed in the skin surface. This is typical of ulcers, for example.

The laser fan-beam pattern reflects this more complex shape. Outside of the wound W the laser fan-beams form generally smooth curves. These curves contain data that reflect the overall shape of the patient's leg L.

Inside the wound W the laser-fan-beams will have a different curvature. Inside the wound W, the curves contain data that reflect the shape of the wound.

From the structured light data obtained from the three laser fan-beams, together with information about the wound boundary, it is possible to establish a model of the surface of the wound W and/or to obtain information such as a wound area, wound depth or wound volume. Various modeling techniques and measurements are discussed in the Applicant's copending application published as US2009/213213, the contents of which are hereby incorporated by reference herein. A model of the leg surface, or other anatomical surface as appropriate, may also be established if desired.

Figure 17:
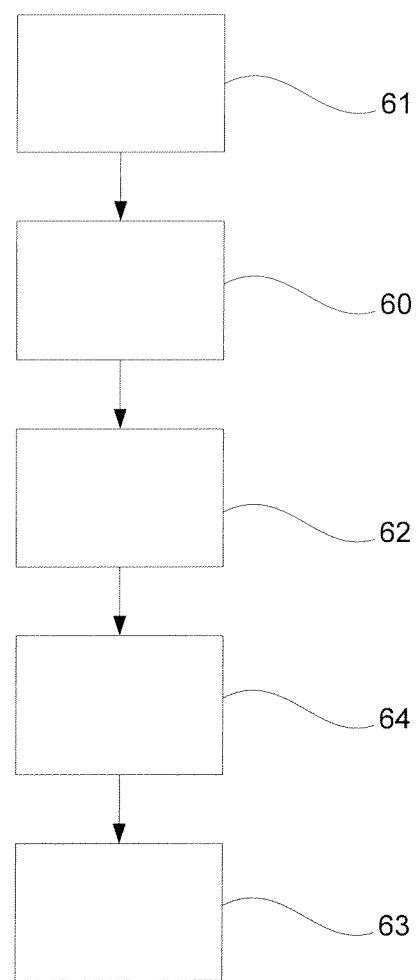
FIG. 17 is a flow diagram illustrating a data capture sequence.

The device 1 captures image data using the camera 5. One example of a capture sequence will now be described with reference to FIG. 17. Other sequences may also be suitable.

In a first step 60 a first image is captured without any laser fan-beams being switched on. This is an image of the skin surface and skin feature (e.g. wound, lesion, mole etc). Optionally this image capture may be preceded by one or more calibration images 61 designed to ensure that the first image is captured with acceptable exposure. The first image may be captured with illumination from the light sources 11, and exposure may be adjusted in the camera 5 or by adjusting the power output of the light sources 11. Alternatively the first image and its associated calibration images, if any, may be captured at a later point in the capture sequence.

In a second step 62 an image is captured with all three laser fan-beams turned on. This structured light image can be processed to obtain the structured light data allowing measurements to be made on the skin feature.

It is not always possible to differentiate unambiguously between the laser fan-beams in the structured light image. This may lead to errors or inaccuracies in any measurements that may be made. In order to address this problem, one or more disambiguation images may also be captured at step 63. Preferably n–1 disambiguation images are captured, where n is the number of laser fan-beams used. Each image is captured with a subset of the laser fan-beams turned on. For example, each disambiguation image may include a single laser fan-beam. The data from the disambiguation images can then be used to identify the different laser fan-beams unambiguously in the structured light image.

As an alternative, a number of structured light images may be captured, each with just one laser fan-beam switched on. This avoids the need for disambiguation images, but could allow mis-registration due to movement between the structured light images.

The structured light images and/or disambiguation images may also be preceded by calibration images at step 64 to ensure correct exposure.

Preferably the images are captured over a very short space of time. This prevents significant movement between the images. In one embodiment, calibration images, the first image, structured light image and disambiguation images may all be captured in less than 1 second, preferably around 0.1-0.5 seconds. Memory, in particular a buffer, may be provided in the device 1 to allow rapid capture of image data. Data may be transferred at a slower rate from the handheld device 1 to an external device.

All images are preferably captured in response to a single user-actuation of the capture switch or button 4.

Thus, in use the device 1 may be directed by a user so that optical axis 7 is approximately aligned with the central region of wound W. The user may use the projected laser stripes to assist in framing, as discussed above. The laser fan-beams or stripes 20, 21, 22 are projected across wound W and the image or images are captured by camera 5. The skilled reader will understand that, due to the fixed angular relationship of the laser fan beams 20, 21, 22 and the optical axis 7 that the three dimensional positions of points along the laser fan beams may be determined from the structured light data. Models of the wound surface and the skin surface may then be developed to fit the three dimensional position data obtained.

The wound surface model and/or skin surface model may be an inelastic surface draped between the three-dimensional coordinates of the structured light elements, or an elastic surface stretched between the three-dimensional coordinates, or a model of the anatomy, or simply a scaled planar projection. A model of the anatomy may be a model retrieved from a library of models, or simply a geometric shape approximating anatomy (a cylinder approximating a leg, for example).

Figure 15:
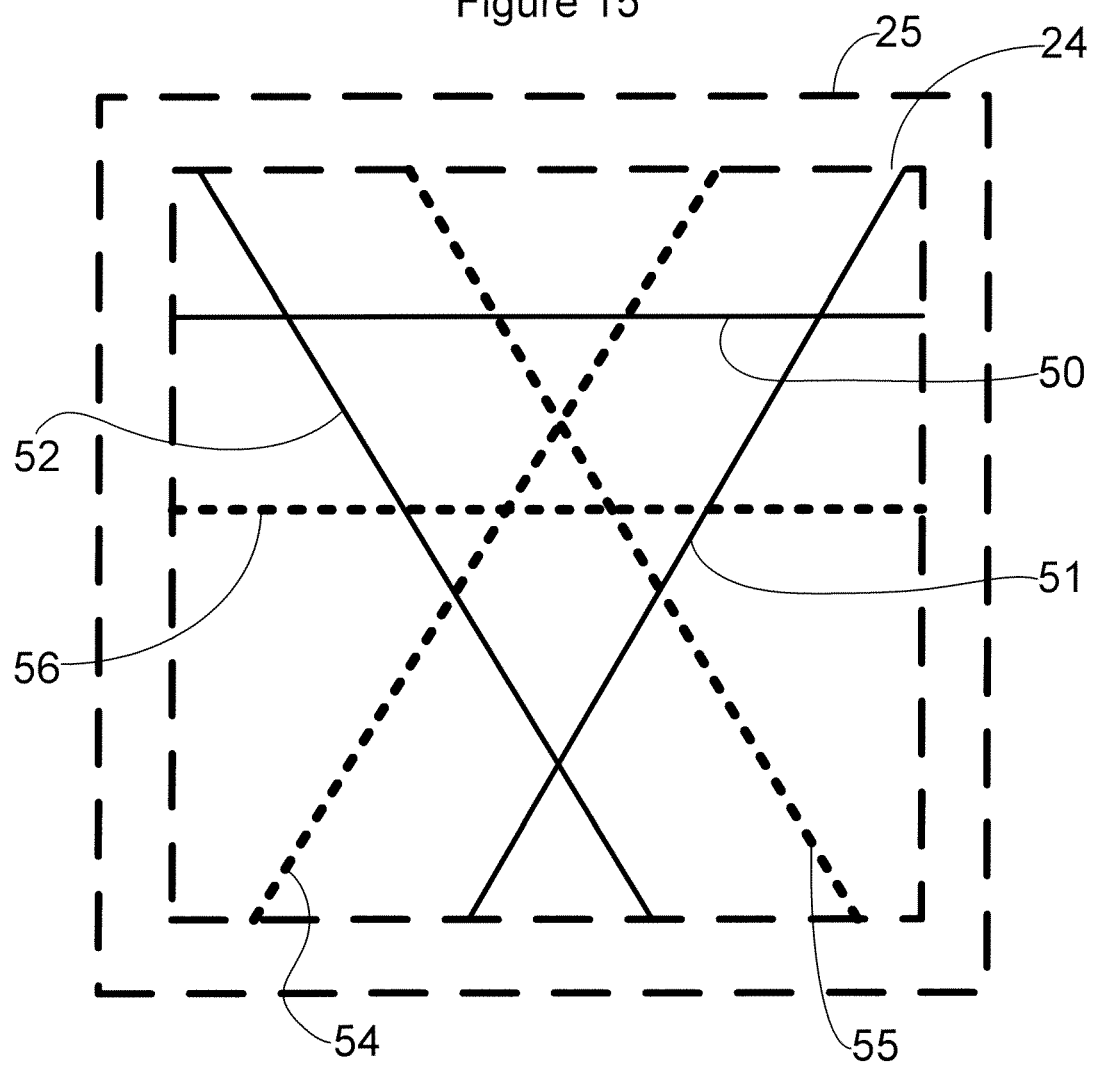
FIG. 15 shows a laser pattern projected onto a surface by a device according to a further embodiment.

FIG. 15 shows a laser pattern projected onto a surface by a device that is a modification of the device of FIG. 1. This device projects two sets of laser beams. In FIG. 15 one set of laser fan-beams 50, 51, 52 is shown in solid line, while a second set of laser fan-beams 54, 55, 56 is shown in dashed line. This is solely for the purposes of clarity. In practice the laser fan-beams may all be the same, or each set may be a different color or frequency.

In the embodiment of FIG. 15, the lasers are arranged such that a crossing point of the first set of laser fan-beams is a first distance from the device, and a crossing point of the second set of laser fan-beams is a second distance from the device. The first distance may correspond to a minimum measurement distance and the second distance to a maximum measurement distance (or the first and second distances are the limits of an optimum measurement range). A user adjusts the distance between the device and the skin such that the skin surface falls between the two crossing points.

Further, the position of the skin surface within the optimum measurement range may be apparent from the laser pattern. In FIG. 15 two triangles are defined by the two sets of laser fan-beams 50, 51, 52 and 54, 55, 56. If the device has two sets of laser projectors mounted together (i.e. two laser projectors at each point 9 in FIG. 7), then the triangles will be inverted with respect to each other (as is the case in FIG. 15) within the optimum measurement range. This is because of the inversion of each triangle with distance, as discussed above with reference to FIGS. 11 and 12. If the triangles are not inverted with respect to each other, then the skin surface is either closer than the nearer crossing point, or more distant than the further crossing point. In other words, when the user sees a predetermined pattern in the form of two triangles inverted with respect to each other, they know that the device is within the optimum measurement range.

Figure 16:
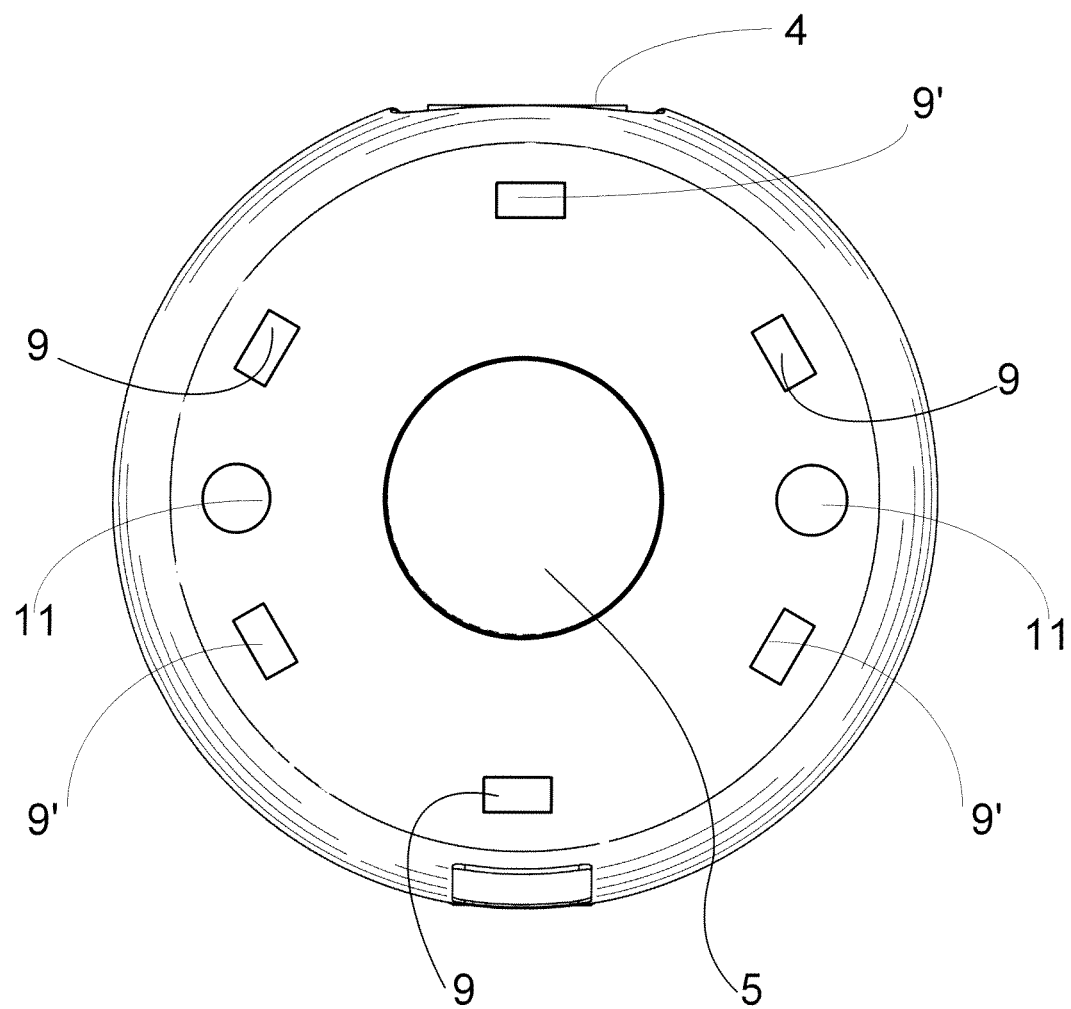
FIG. 16 shows a skin measuring or monitoring device according to a further embodiment.

In a further embodiment shown in FIG. 16, two sets of laser fan-beam projectors are offset, with a first set of projectors 9 positioned as in FIG. 7 and a second set of projectors 9' positioned in-between the projectors 9. In the embodiment of FIG. 16, each set is a set of three laser fan-beam projectors and the lasers are arranged such that a crossing point of the first set of laser fan-beams is a first distance from the device, and a crossing point of the second set of laser fan-beams is a second distance from the device. The first distance may correspond to a minimum measurement distance and the second distance to a maximum measurement distance (or the first and second distances are the limits of an optimum measurement range).

In this embodiment the triangles will be inverted when the skin surface is outside of the optimum measurement range. If the shapes of the two triangles are the same (i.e. not inverted) then the skin surface is within the optimum measurement range. In other words, when the user sees a predetermined pattern in the form of two triangles with the same orientation, they know that the device is within the optimum measurement range.

Figure 18:
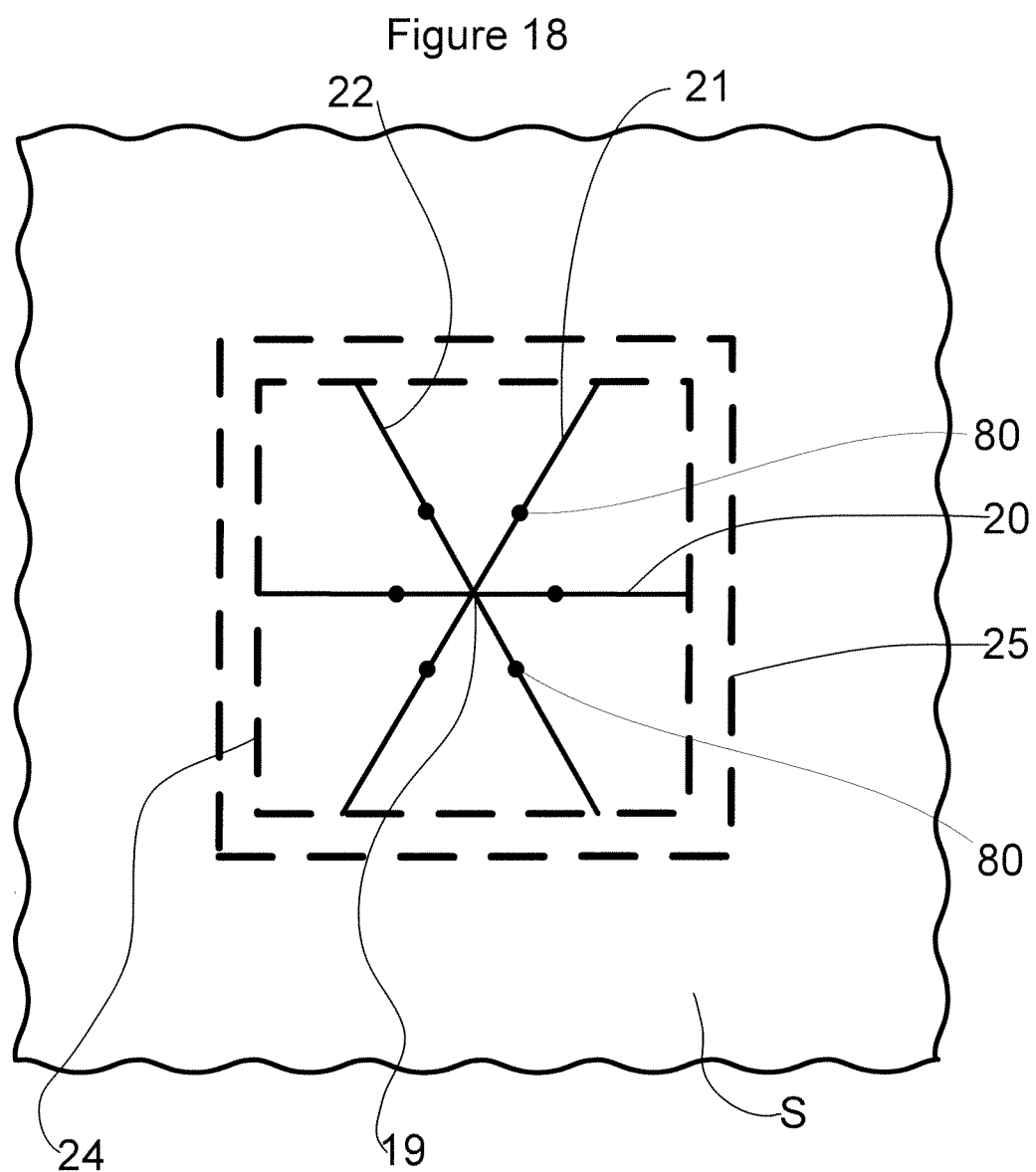
FIG. 18 shows a laser pattern projected onto a surface by a device according to yet a further embodiment.
Figure 19:
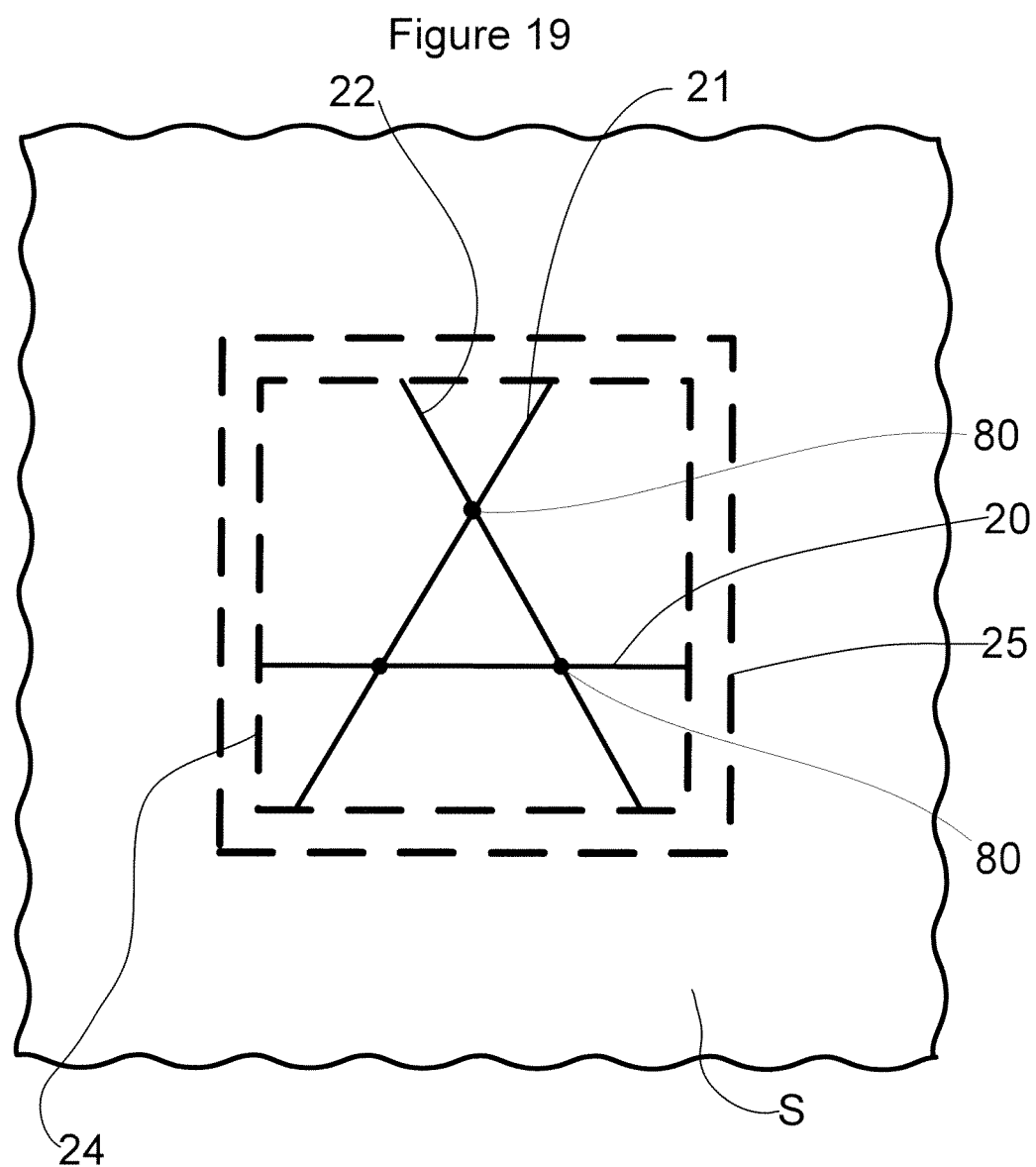
FIG. 19 shows a further laser pattern projected onto a surface by the device of the embodiment of FIG. 18.
Figure 20:
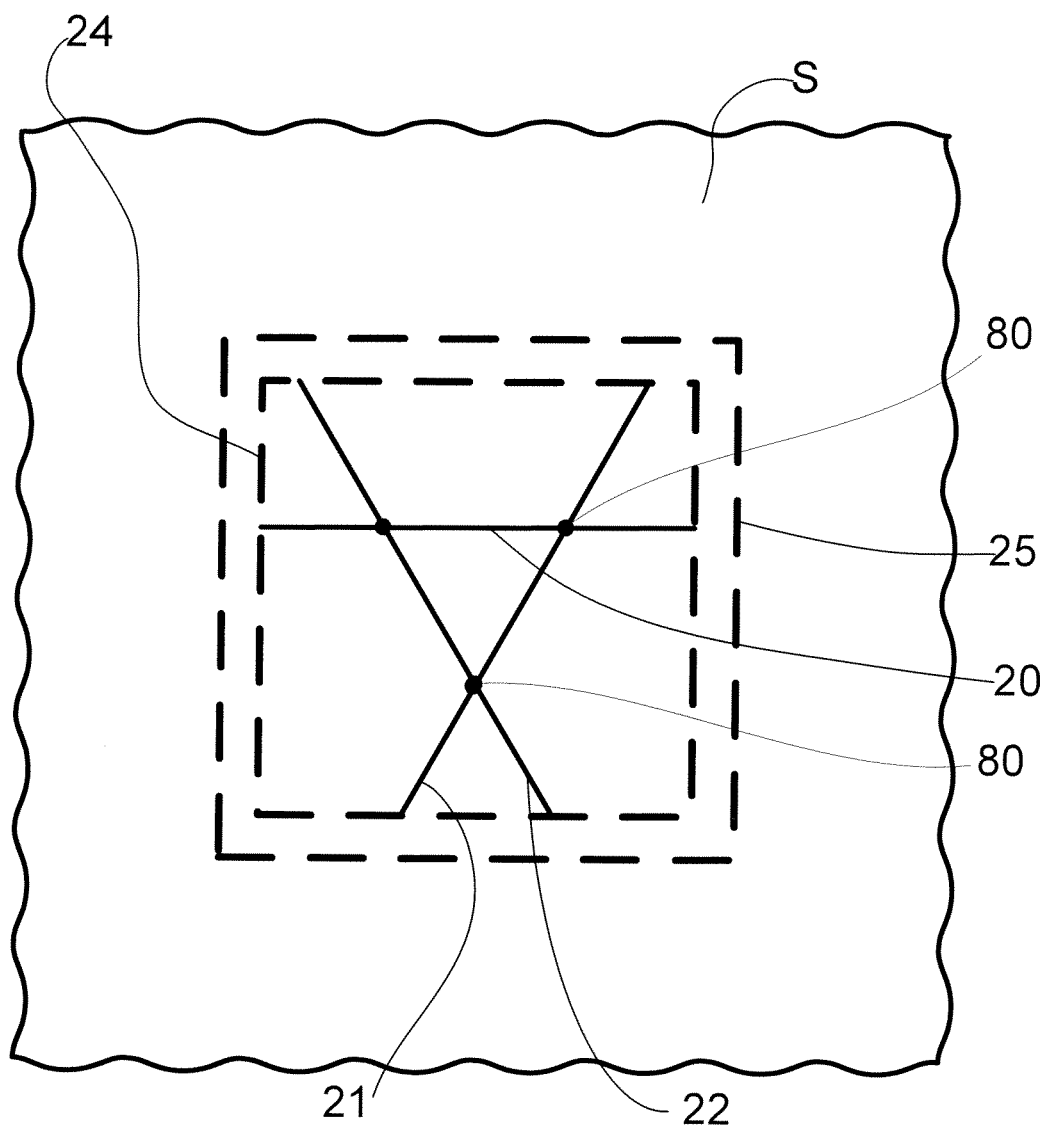
FIG. 20 shows a further laser pattern projected onto a surface by the device of the embodiment of FIG. 18.

In another embodiment shown in FIG. 18, a single set of three laser fan-beam projectors is provided, with the beams again arranged to cross in front of the device. In this embodiment the fan-beam angle ∝ and the angle with respect to the optical axis 7 are such that the three laser stripes cross at a crossing point 19 at an optimum measurement range. At other ranges the lines will form triangles. Further, the laser stripes of this embodiment may be projected together with small markers 80, such as laser spots or some other identifiable feature, such as dots, small lines crossing the laser stripe, small gaps in the laser stripe etc. The fan-beam angle and angle to the optical axis may be arranged such that when the markers 80 on different laser stripes align with each other, the device is at the outer limit of the optimum measurement range. Thus, FIG. 19 shows the laser pattern at the lower limit of the optimum measurement range, while FIG. 20 shows the laser pattern at an upper limit of the optimum measurement range. In this embodiment, when the user sees a predetermined pattern in the form of the lines crossing at a crossing point (as in FIG. 18) the user will know that the device is at or near an optimum measurement distance from the skin surface; or if the user sees a predetermined pattern in the form of a triangle, with markers 80 positioned outside the corners of the triangle the user will know that the device is within an optimum measurement range. If the markers 80 are inside the corners of the triangle then the device is outside the optimum measurement range. As with other embodiments, the equilateral triangle pattern is shown for illustrative purposes and corresponds to projection onto a flat surface perpendicular to the optical axis. More complex patterns result from projection onto more complex surfaces.

Figure 14:
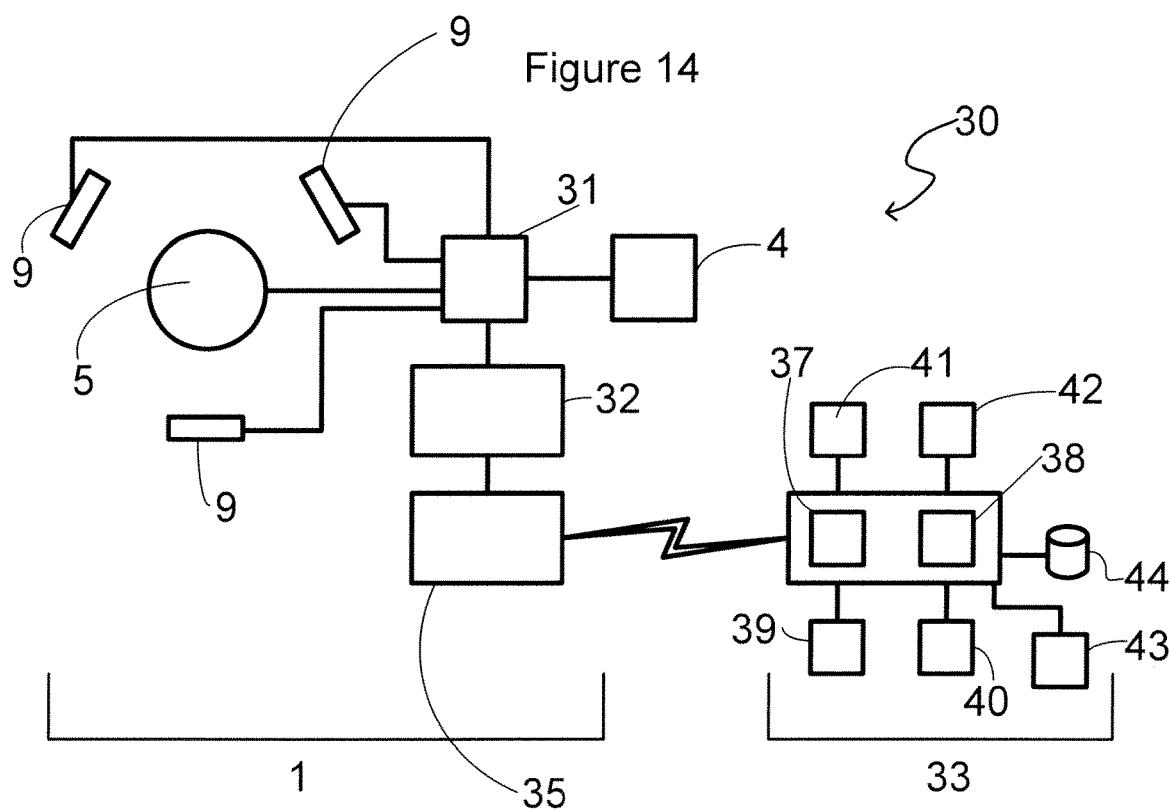
FIG. 14 shows a skin monitoring and measuring system according to one embodiment.

FIG. 14 shows the device 1 that may form part of a broader system 30. The device 1 includes a controller 31 that controls the camera 5, structured light projectors 9 and the light sources 11 (not shown in FIG. 14). The controller 31 is configured to control these components in response to user-actuation of the capture switch 4. The data generated by these devices is passed to a buffer memory 32, which holds the data until it can be passed from the device to an external computer 33.

The device 1 may be connected to the external computer by any suitable mechanism. Wired connections, such as USB or Firewire connections, may be used. The device may be configured to dock in a physical dock connected to the external computer 33. Alternatively, wireless connections may be used, including e.g. Bluetooth.

In any case, the device 1 includes a communications port 35 arranged for wired or wireless communications. In the embodiment shown in FIGS. 1 to 7 the communications port 35 is a USB port. Data is transmitted from the communications port 35 to the external computer 33.

The external computer 33 includes a processor 37 and memory 38. The external computer may also include a display 39 and output devices such as printers 40 and the like. The external computer 33 may include user input devices such as keyboard 41 and mouse 42. A stylus 43 may also be provided. The external computer 33 may be connected to a database 44.

The external computer may be any suitable computer or collection of computer devices, including: PDAs, Smartphones, Personal Computers, Laptops, Tablet computers etc.

Thus the device 1 is configured to capture data and transmit that data to the external computer 33. In one embodiment the device 1 does not perform any processing of the data, but simply passes it to the external computer 33. The device 1 preferably has no display. A user may capture data using the device 1 but analyses the data using the external computer 33.

Desirably a user may be permitted to manually define a skin feature boundary. This may be done using a mouse 42 or other pointing device, or the stylus 43. The boundary may be used to assist in developing a model of the wound surface and/or in determination of wound depth, area and/or volume. Utilizing manual input of the outline avoids the need for complex image processing capabilities. Further, this approach utilizes human image processing capabilities to deter mine the outline where automated approaches may be less effective.

Data may be maintained in the database 44 and used for monitoring of the skin feature over time. For example, records gathered over a time period can be used to monitor the healing of a wound or ulcer, or the growth of a potentially cancerous mole. Alerts may be generated if healing or growth exceeds a threshold.

The external computer may communicate with a central server that maintains the database 44. In this way data captured by a number of devices 1 may be centrally stored in a convenient manner.

This centralized system allows appropriate categorizing and storage of data for future use. For example, by mining historical data from the database it is possible to analyze the efficacy of a particular treatment or to compare different treatments. Statistical trends of conditions, treatments and outcomes can be monitored. This data can be used to suggest a particular treatment, based on a set of symptoms exhibited by a particular patient. Data can provide predictions for wound healing. Where actual healing differs from the prediction by more than a threshold, the system may issue an alert.

A healthcare provider may use the data to audit efficiency of its whole organization, departments within the organization or even individual workers. Historical data may be compared with historical worker schedules to determine whether workers are performing all tasks on their schedules. Efficiencies of different workers may be compared.

Data may be stored in a patient record along with measurement information (wound area, wound depth, wound volume etc). Where previous information has been stored comparative measurements may be made and an indication of improvement or deterioration may be provided. Data may be sent directly to a central database or distributed to medical professionals for evaluation. This allows an expert to review information obtained in the field and provide medical direction while the health practitioner is visiting the patient. The historic record allows patient progress to be tracked and re-evaluated, if necessary.

Measurements of other wound information may also be made. The color of the wound and the size (linear dimension, area or volume) of particular colored regions may also be calculated. These measurements may require a color reference target to be placed within the image capture area for accurate color comparison to be made.

There are thus provided methods of measuring wounds that are simple, inexpensive, repeatable and may be performed remotely, without contacting the skin surface. The methods may utilize human image processing capabilities to minimize the processing requirements. The methods do not require the placement of articles near the wound. The methods allow historical comparison of a wound. The device 1 is portable with relatively low processing requirements and enables records to be sent wirelessly or over a wired connection for evaluation and storage.

Further devices, such as GPS units, auxiliary sensors, temperature sensors, pH sensors, moisture sensors, odor sensors, optical probes, fluorescence probes and/or Doppler ultrasound probes, may be used in combination with the device 1, as discussed in the Applicant's copending application published as US2009/213213.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A method of capturing data concerning an anatomical surface feature on a patients skin surface, using a camera and a projection arrangement in fixed relation to each other, the method including:
 projecting visible light from the projection arrangement onto the patient's skin surface;
 guiding a user to position the camera within an optimum distance range relative to the anatomical surface feature by:
  a. forming a first shape on the skin surface with the visible light when the camera is outside of an optimum distance range from the anatomical surface feature; and
  b. forming a second shape different from the first shape only when the camera is within the optimum distance range from the anatomical surface feature so that the user may position the camera within the optimum distance range by reference to the shape of the visible light on the skin surface; and
 capturing image data of the anatomical surface feature with the camera.

2. The method of claim 1 wherein projecting visible light includes projecting a plurality of laser fan beams.

3. The method of claim 1 wherein projecting visible light includes projecting at least three laser fan beams.

4. The method of claim 1 wherein projecting visible light includes projecting at least three intersecting laser fan beams.

* * * * *

UNITED STATES PATENT AND TRADEMARK OFFICE
CERTIFICATE OF CORRECTION

PATENT NO. : 11,850,025 B2
APPLICATION NO. : 17/100615
DATED : December 26, 2023
INVENTOR(S) : William Richard Fright et al.

It is certified that error appears in the above-identified patent and that said Letters Patent is hereby corrected as shown below:

On the Title Page

Item (71) Column 1, Line 1, delete "Limited" and insert -- Limited, (NZ) --, therefor.

On page 7, Item (56) Column 1, Line 2, delete "Eoidemiol" and insert -- Epidemiol --, therefor.

On page 7, Item (56) Column 1, Line 32, delete ""JWound" and insert -- J Wound --, therefor.

On page 7, Item (56) Column 1, Line 37, delete "patientcom," and insert -- patient com, --, therefor.

On page 7, Item (56) Column 1, Line 37, delete "AdvSkin" and insert -- Adv Skin --, therefor.

On page 7, Item (56) Column 2, Line 9, delete "Intemational" and insert -- International --, therefor.

On page 7, Item (56) Column 2, Line 32, delete "ofTNP" and insert -- of TNP --, therefor.

On page 7, Item (56) Column 2, Line 53, delete "Lasres" and insert -- Lasers --, therefor.

On page 7, Item (56) Column 2, Line 57, delete "No. I." and insert -- No. 1. --, therefor.

On page 7, Item (56) Column 2, Line 61, delete "comparisan" and insert -- comparison --, therefor.

On page 8, Item (56) Column 1, Line 4, delete "Lewies," and insert -- Lewis, --, therefor.

On page 8, Item (56) Column 1, Line 21, delete "2004)." and insert -- 2004]. --, therefor.

On page 8, Item (56) Column 1, Line 50, delete "ald" and insert -- aid --, therefor.

On page 8, Item (56) Column 1, Line 52, delete "onMar." and insert -- on Mar. --, therefor.

Signed and Sealed this
Eleventh Day of June, 2024

Katherine Kelly Vidal
*Director of the United States Patent and Trademark Office*

CERTIFICATE OF CORRECTION (continued)
U.S. Pat. No. 11,850,025 B2

On page 8, Item (56) Column 1, Line 52, delete "2008)." and insert -- 2008]. --, therefor.

On page 8, Item (56) Column 1, Line 64, delete "1 1P56," and insert -- 11P56, --, therefor.

On page 8, Item (56) Column 2, Line 24, delete "Woundcare,"" and insert -- Wound care," --, therefor.

On page 8, Item (56) Column 2, Line 62, delete "SI-S28," and insert -- S1-S28, --, therefor.

On page 9, Item (56) Column 1, Line 43, delete "No. IO." and insert -- No. 10. --, therefor.

On page 9, Item (56) Column 1, Line 60, delete "No. I." and insert -- No. 1. --, therefor.

On page 9, Item (56) Column 2, Line 21, delete "Wal" and insert -- Wai --, therefor.

In the Claims

Column 11, Line 13, delete "deter mine" and insert -- determine --, therefor.